(12) United States Patent
Rush et al.

(10) Patent No.: US 8,757,386 B2
(45) Date of Patent: Jun. 24, 2014

(54) ANALYTE TEST STRIP CONTAINERS AND INSERTS

(75) Inventors: Benjamin M. Rush, Oakland, CA (US); Craig W. Sharp, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 519 days.

(21) Appl. No.: 12/895,502

(22) Filed: Sep. 30, 2010

(65) Prior Publication Data

US 2012/0080330 A1    Apr. 5, 2012

(51) Int. Cl.
*B65D 85/38* (2006.01)

(52) U.S. Cl.
USPC .............................. 206/765; 206/305; 206/804

(58) Field of Classification Search
USPC ......... 206/804, 740, 738, 739, 765, 761, 540, 206/814, 817, 800, 305; 220/527, 528, 220/23.9; 422/939; 53/473, 475, 443
See application file for complete search history.

(56) References Cited

U.S. PATENT DOCUMENTS

| | | | | |
|---|---|---|---|---|
| 2,487,107 A * | 11/1949 | D'Andrea | ....................... | 312/73 |
| 3,081,867 A * | 3/1963 | Corey | ........................... | 206/248 |
| 4,444,308 A * | 4/1984 | MacEwen | ...................... | 206/249 |
| 4,464,552 A * | 8/1984 | Pawlowski | ..................... | 206/569 |
| 5,154,303 A * | 10/1992 | Jordan | ........................ | 220/23.86 |
| 5,312,011 A * | 5/1994 | Fischer | .......................... | 220/528 |
| 5,373,945 A * | 12/1994 | Niehaus | ........................ | 206/445 |
| 5,551,591 A * | 9/1996 | Laib | ............................... | 220/528 |
| 5,723,085 A | 3/1998 | Abrams et al. | | |
| 5,911,937 A | 6/1999 | Hekal | | |
| 6,047,842 A * | 4/2000 | Feidt | ........................... | 220/23.88 |
| 6,071,391 A | 6/2000 | Gotoh et al. | | |
| 6,102,233 A * | 8/2000 | Waugh | ........................ | 220/23.86 |
| 6,143,164 A | 11/2000 | Heller et al. | | |
| 6,592,745 B1 | 7/2003 | Feldman et al. | | |
| 6,616,819 B1 | 9/2003 | Liamos et al. | | |
| 6,893,545 B2 | 5/2005 | Gotoh et al. | | |
| 7,059,492 B2 * | 6/2006 | Giraud et al. | .................. | 220/834 |
| 7,172,728 B2 * | 2/2007 | Otake | ........................... | 422/404 |
| 8,066,957 B2 * | 11/2011 | Chan et al. | ..................... | 422/401 |
| 2004/0065669 A1 * | 4/2004 | Giraud et al. | ................. | 220/839 |
| 2006/0025662 A1 | 2/2006 | Buse et al. | | |
| 2006/0091006 A1 | 5/2006 | Wang et al. | | |
| 2006/0118570 A1 * | 6/2006 | Fowler et al. | .................... | 221/65 |
| 2007/0034630 A1 * | 2/2007 | Lancesseur et al. | .......... | 220/281 |
| 2007/0068807 A1 | 3/2007 | Feldman et al. | | |
| 2007/0095661 A1 | 5/2007 | Wang et al. | | |
| 2007/0108048 A1 | 5/2007 | Wang et al. | | |
| 2007/0199818 A1 | 8/2007 | Petyt et al. | | |
| 2008/0066305 A1 | 3/2008 | Wang et al. | | |
| 2008/0102441 A1 | 5/2008 | Chen et al. | | |

(Continued)

*Primary Examiner* — Jacob K Ackun
(74) *Attorney, Agent, or Firm* — Edward J. Baba; Shweta Chandra; Bozicevic, Field & Francis LLP

(57) ABSTRACT

In some aspects of the present disclosure, analyte test strip containers, and methods of manufacturing the same, are provided. The analyte test strip containers may include an interior side of a base that varies in height. In some aspects of the present disclosure, inserts are provided. The inserts serve to provide the cavity floor with a varying height with respect to a longitudinal axis of the container. In some aspects of the present disclosure, analyte test strip container systems, and methods of making the same, are provided. The analyte test strip container systems include a container and insert that situates within the container to provide a cavity floor that varies in height.

24 Claims, 11 Drawing Sheets

(56) References Cited

U.S. PATENT DOCUMENTS

| | | |
|---|---|---|
| 2008/0148873 A1 | 6/2008 | Wang et al. |
| 2008/0267823 A1 | 10/2008 | Wang et al. |
| 2009/0095625 A1 | 4/2009 | Forrow et al. |
| 2009/0255811 A1 | 10/2009 | Forrow et al. |
| 2010/0000905 A1* | 1/2010 | Wang et al. ............ 206/569 |
| 2010/0043359 A1* | 2/2010 | Skiffington et al. ............ 53/471 |
| 2010/0325868 A1 | 12/2010 | Wang et al. |
| 2011/0056951 A1* | 3/2011 | Wooldridge ............ 220/495.01 |
| 2011/0127175 A1* | 6/2011 | Chan et al. ............ 206/204 |
| 2011/0127269 A1* | 6/2011 | Bucholtz et al. ............ 220/378 |
| 2011/0253736 A1* | 10/2011 | Fujimoto et al. ............ 221/199 |
| 2011/0263006 A1* | 10/2011 | Chan et al. ............ 435/287.1 |

\* cited by examiner

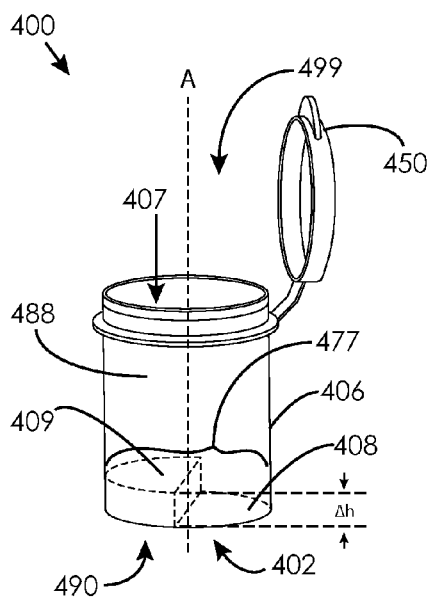
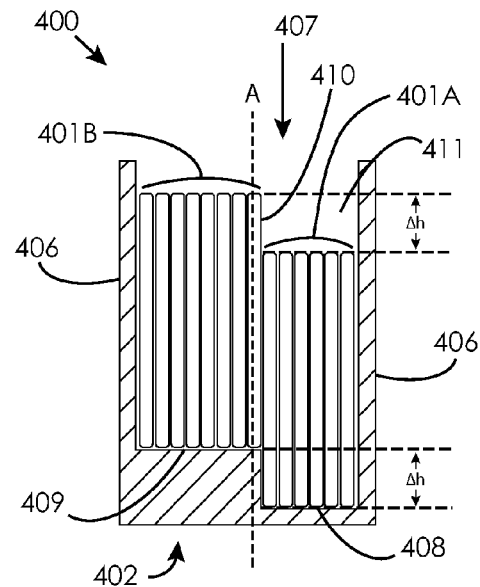
FIG. 5A  FIG. 5B
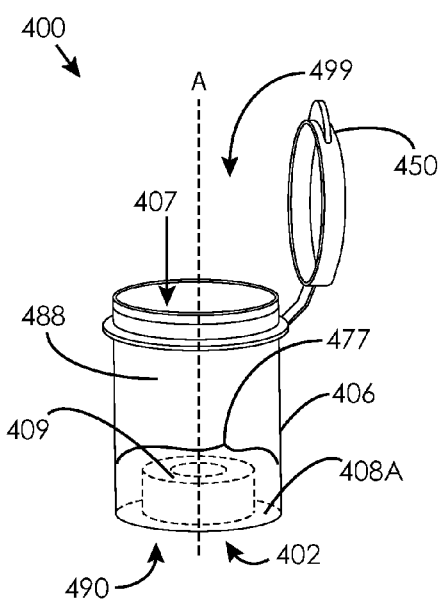
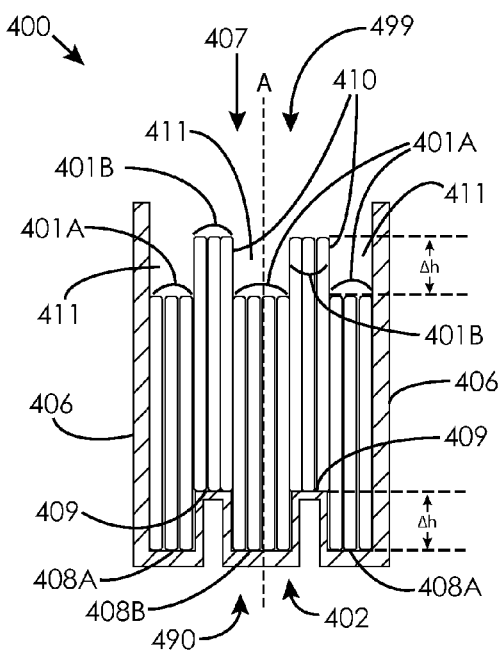
FIG. 6A  FIG. 6B

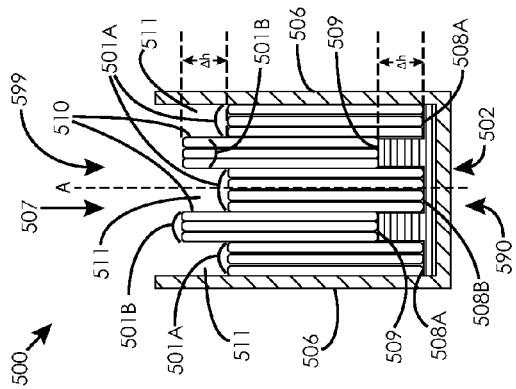
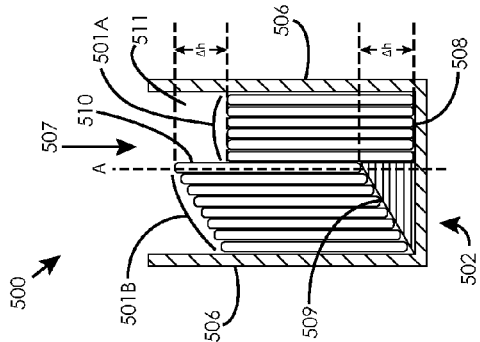
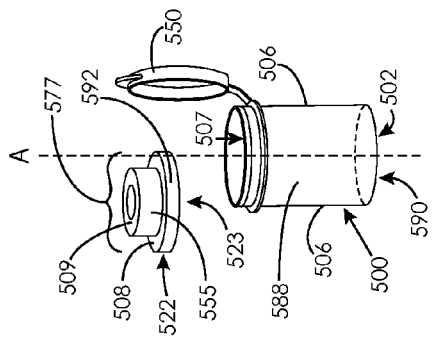
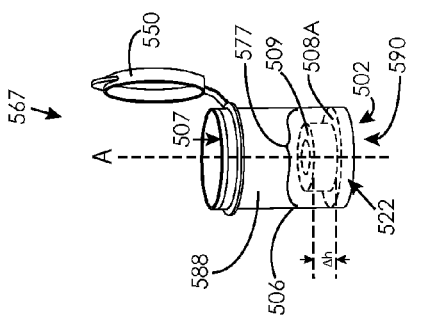
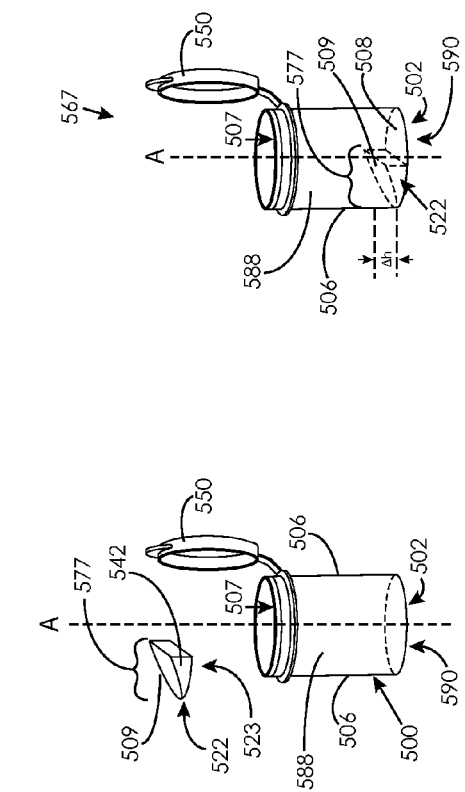

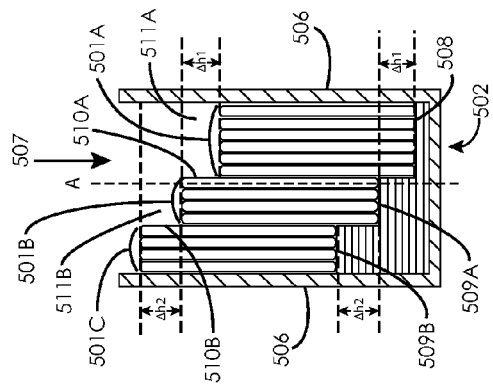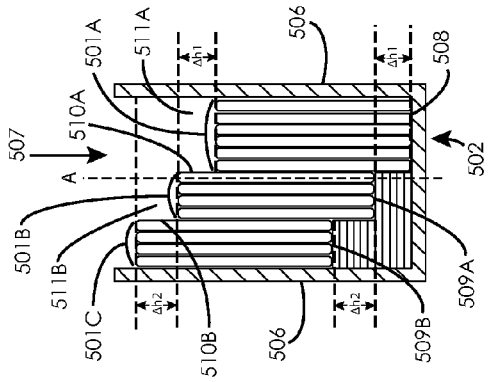
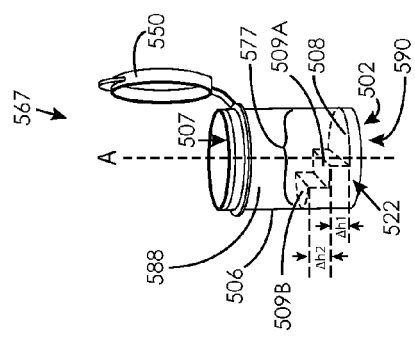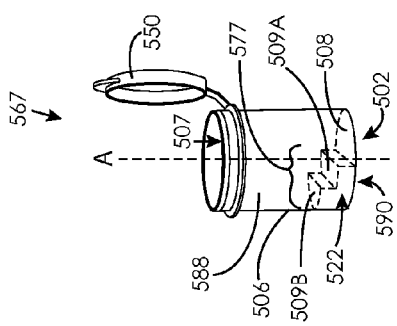
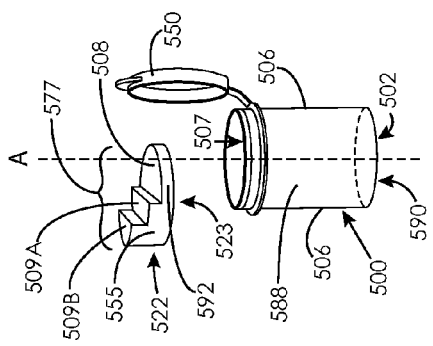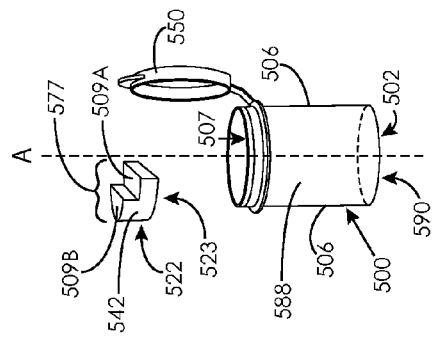

US 8,757,386 B2

ANALYTE TEST STRIP CONTAINERS AND INSERTS

BACKGROUND OF THE INVENTION

Analyte test strips have been used with analyte test meters to provide measurements of analyte levels of a sample. One common application is the determination of blood glucose levels for diabetics. Typically, a diabetic obtains a test strip, inserts it into a glucose meter, pricks his finger using a lancet, and then applies a blood sample to the test strip so the meter may provide a blood glucose measurement.

A number of test strips are usually stored together in a vial having a cap to close the vial. When a test strip is needed, the patient opens the container and inserts a finger or two into the container to grab the test strip. Typically, the vial is usually small and includes a large number of small test strips. If too many analyte test strips are included in the vial, obtaining a single test strip from the vial can pose a small challenge for some users (e.g., diabetic patients). With too many test strips disposed at approximately the same height within the container, the ends of the analyte test strips act collectively as a sort of barrier or surface that prevents the user from easily grabbing a test strip. The more test strips in the container, the less space exists between the test strips for a user to insert a finger tip to grab a test strip. This often leads to the patient trying to forcefully push or wedge their finger tip into a space between test strips to extract a test strip. This may prove difficult and frustrating as well, and may potentially lead to damaging test strips. Users may also find that it is easier to tip or shake the vial to slide multiple test strips partially or completely out of the vial to obtain a test strip. Such techniques may unnecessarily expose other test strips to potential contaminants outside the vial, and may also lead to the patient spilling one or more test strips.

SUMMARY OF THE INVENTION

In some aspects of the present disclosure, analyte test strip containers, and methods of manufacturing the same, are provided. The analyte test strip containers may include an interior side of a base that varies in height with respect to a longitudinal axis of the container. In some aspects of the present disclosure, inserts are provided. The inserts serve to provide the cavity floor with a varying height with respect to a longitudinal axis of the container. In some aspects of the present disclosure, analyte test strip container systems, and methods of making the same, are provided. The analyte test strip container systems include a container and insert that situates within the container to provide a cavity floor that varies in height with respect to a longitudinal axis of the container.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 5A and 5B illustrate a perspective and a partial cross-sectional view of a container, respectively, according to certain embodiments;

FIGS. 6A and 6B illustrate a perspective and a partial cross-sectional view of a container, respectively, according to certain embodiments;

FIG. 13A illustrates a perspective view of an analyte test strip container and insert before the insert is situated within the cavity of the container, according to certain embodiments;

FIGS. 13B and 13C illustrates a perspective and partial cross-sectional view of an analyte test strip container system shown in FIG. 12A after the insert is situated within the cavity and analyte test strips disposed thereon, according to certain embodiments;

FIG. 14A illustrates a perspective view of an analyte test strip container and insert before the insert is situated within the cavity of the container, according to certain embodiments;

FIGS. 14B and 14C illustrates a perspective and partial cross-sectional view of an analyte test strip container system shown in FIG. 13A after the insert is situated within the cavity and analyte test strips disposed thereon, according to certain embodiments;

FIG. 17A illustrates a perspective view of an analyte test strip container and insert before the insert is situated within the cavity of the container, according to certain embodiments;

FIGS. 17B and 17C illustrates a perspective and partial cross-sectional view of an analyte test strip container system shown in FIG. 16A after the insert is situated within the cavity and analyte test strips disposed thereon, according to certain embodiments;

FIG. 18A illustrates a perspective view of an analyte test strip container and insert before the insert is situated within the cavity of the container, according to certain embodiments;

FIGS. 18B and 18C illustrates a perspective and partial cross-sectional view of an analyte test strip container system shown in FIG. 17A after the insert is situated within the cavity and analyte test strips disposed thereon, according to certain embodiments;

DETAILED DESCRIPTION OF THE INVENTION

Figure 1:
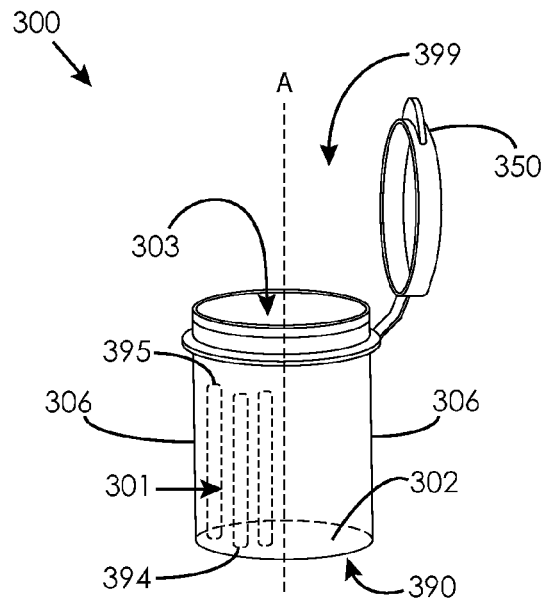
FIG. 1 illustrates a perspective view of a container that stores a plurality of analyte test strips, according to the prior art.

Before the present inventions are described, it is to be understood that this invention is not limited to particular aspects described, as such may, of course, vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a supporting surface" may include a plurality of supporting surfaces and reference to "the supporting surface" may include reference to one or more supporting surfaces and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

To facilitate explanation of the analyte test strip containers, inserts, analyte test strip container systems, and components thereof, references are made herein to a proximal and distal end of the container. The term "proximal end of the container" is used herein to refer generally to the bottom end of the container as illustrated in the perspective views of the container in the figures. For example, in the containers shown in the figures, the base is at a proximal end of the container. Accordingly, the "distal end of the container" is used herein to refer generally to the top end of the container as illustrated in the perspective views of the container in the figures. For example, in the containers shown in the figures, the opening of the container is at a distal end of the container.

Furthermore, it should be appreciated that various components of the containers, inserts, and test strips described herein have a "proximal" end, side, tip, etc., and a "distal" end, side, tip, etc. The "proximal" end, side, tip, etc., of a component is used herein to refer generally to the end, side, tip, etc., of the component that is closest to the proximal end of the container as illustrated in the perspective views of the container in the figures. Accordingly, the "distal" end, side, tip, etc., of a component is used herein to refer generally to the end, side, tip, etc., of the component that is closest to the distal end of the container as illustrated in the perspective views of the container in the figures. For example, the proximal end of the analyte test strip is the end of the test strip that is closest to the base when the analyte test strip is disposed in the container, and the distal end of the analyte test strip is the end of the analyte test strip that is closest to the opening of the container when the analyte test strip is disposed in the container. As another example, the proximal side of an insert is the side of the insert that faces the proximal end of the container (e.g., faces the base of the container) when the insert is situated within the container, and the distal side of the insert (referred to herein as the "interior side of the insert") is the end of the insert that faces the top of the container (e.g., faces the opening).

Furthermore, a longitudinal axis A is referred to herein and illustrated within the figures to extend through the proximal and distal ends of the container—e.g., through the base and opening of the container. The terms "longitudinal distance" and "length" are used herein to refer generally to a longitudinal distance along the longitudinal axis of the container. Furthermore, the term "height" and "longitudinal height" are used herein to refer generally to a longitudinal distance along the longitudinal axis of the container with respect to the proximal end of the container such that a higher "height' refers to a position along the longitudinal axis A that is further from the proximal end of the container. Moreover, references to a "raised surface" or a "higher surface" (e.g., with respect to another surface) are used herein to refer to a surface that is at a position along the longitudinal axis A that is further from the proximal end of the container (e.g., than the other surface). Similarly, references to a "lower surface" (e.g., with respect to another surface) is used herein to refer to a surface that is at a position along the longitudinal axis A that is closer to the proximal end of the container (e.g., than the other surface).

Furthermore, it should be appreciated that various kinds, sizes, or shapes of analyte tests strips may be stored within the containers of the present disclosure. Example analyte test strips may include FREESTYLE® and FREESTYLE LITE™ test strips sold by ABBOTT DIABETES CARE Inc. In one example, the analyte test strips are used to test glucose levels for diabetic patients. In addition to the embodiments specifically disclosed herein, the containers of the present disclosure can be configured to work with a wide variety of analyte sensors, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. Nos. 6,616,819; 6,143,164; 6,592,745; 6,071,391 and 6,893, 545; the disclosures of which are each incorporated by reference.

FIG. 1 illustrates a perspective view of a container that stores a plurality of analyte test strips, according to the prior art. Container 300 is shown having a flat (also referred to herein as "planar") and level circular base 302 at a proximal end 390 of the container 300, an opening 303 of the container 300 at a distal end 399, and a sidewall 306 extending from the base 302 to the opening 303. A longitudinal axis A is illustrated as dotted line A and extends through the base 302 and opening 303. Container 300 also includes a cap 350 at the distal end 399 that fits over the opening 303 to close the container 300. A plurality of analyte test strips 301 are held in the container 300 with a proximal end 394 of the test strips disposed on the planar and level circular base 302 and a distal end 395 of the test strips facing the opening 303 of the container 300.

Figure 2:
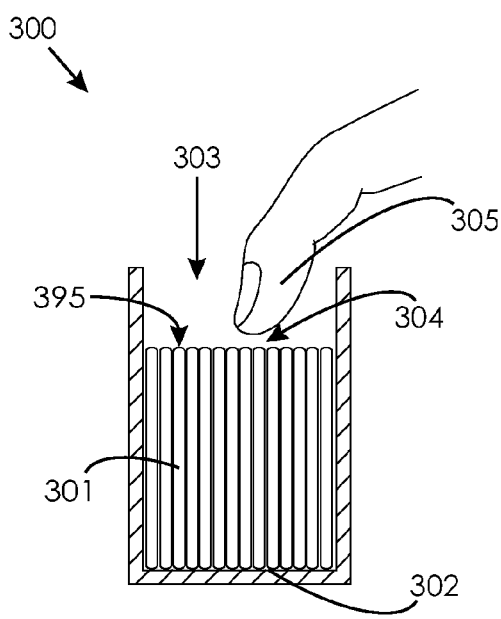
FIG. 2 illustrates a partial cross-sectional view of the container shown in FIG. 1 when the container is full of a plurality of analyte test strips, according to the prior art.

FIG. 2 illustrates a partial cross-sectional view of the container shown in FIG. 1 when the container is full of a plurality of analyte test strips, according to the prior art. The analyte test strips 301 are shown disposed on the planar and level circular base 302 of the container 300. Because the base 302 is generally planar and level, the analyte test strips 301 are disposed within the container 300 at approximately the same height with each of the distal ends 395 of the analyte test strips 301 at approximately the same height within the container 300. The distal ends 395 of the test strips are generally adjacent one another, providing very little space 304 between the plurality of test strips 301. With too many test strips 301 disposed at approximately the same height within the container, the ends 395 of the analyte test strips act collectively as a sort of barrier or surface that prevents the user from easily grabbing a test strip. Because the space 304 between each test strip is relatively small with respect to a finger tip 305, the user may find it very difficult to grip or grab a test strip with a finger 305 to pull it out of the container 300.

Figure 3:
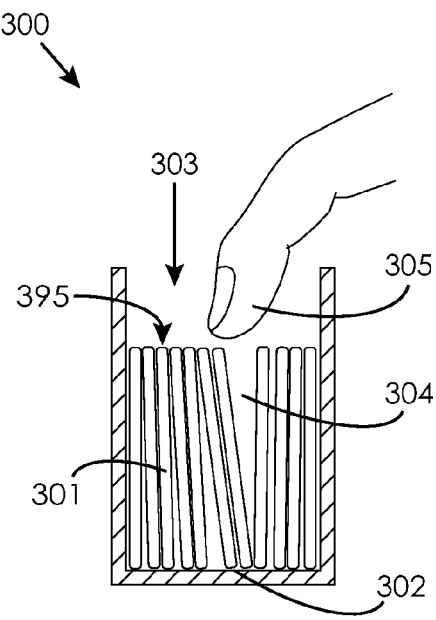
FIG. 3 illustrates a partial cross sectional view of the container shown in FIG. 1 with less test strips than shown in the container of FIG. 2 but still generally full, according to the prior art.

FIG. 3 illustrates a partial cross sectional view of the container shown in FIG. 1 with less test strips than shown in the container of FIG. 2 but still generally full, according to the prior art. As shown, container 300 has a plurality of analyte test strips 301 disposed within the container 300 on the planar and level circular base 302. The analyte test strips 301 are disposed within the container 300 at approximately the same height with each distal end 395 of the analyte test strips 301 at the same height. Space 304 is larger than shown in FIG. 2 because there are less analyte test strips 301 disposed within container 300. However, space 304 is still too small with respect to a finger tip 305 to allow the finger tip 305 to insert within space 304 and easily grip or grab a test strip to pull it out of the opening 303 container 300.

In some aspects of the present disclosure, analyte test strip containers are provided. The analyte test strip containers store a plurality of analyte test strips in a manner that makes it easy for a user to grab an analyte test strip from the container even when the container is generally full or completely full of analyte test strips. The analyte test strip containers may comprise, for example, a base and one or more sidewalls extending from the base. The one or more sidewalls and the base form a cavity having an opening at a distal end and the interior side of the base at a proximal end. As such, the interior side of the base forms the cavity floor and varies in height with respect to a longitudinal axis extending through the base and opening. The term "interior side of the base" is used herein to refer generally to the distal side of the base that faces the opening of the container or cavity. It should be appreciated that the terms "opening of the container" and "opening of the cavity" are used interchangeably herein.

In certain embodiments, a container includes one sidewall that extends from the base. For example, a single sidewall may extend from the perimeter of a circular or elliptical shaped base (e.g., a cylindrical shaped container). In other embodiments, a container includes multiple sidewalls extending from the base. For example, the base may be polygonal shaped with a sidewall extending from each side of the polygon (e.g., a square base and rectangular shaped container). It should be appreciated that the container may have any variety of shaped bases with one more sidewalls extending therefrom.

In certain embodiments, the interior side of the base comprises more than one supporting surface that makes the interior side of the base vary in height with respect to the longitudinal axis. The term "supporting surface" is used herein to mean a surface that is used to support analyte test strips when disposed within the container. For example, the interior side of the base may comprise a first supporting surface to support a first plurality of analyte test strips and a second supporting surface to support a second plurality of analyte test strips. For example, the first supporting surface may be half of the interior side of a circular base and the second supporting surface may be the other half of the interior side of the circular base that is raised in height above the first supporting surface. In this way, a first plurality of analyte test strips may be disposed on the first supporting surface and a second plurality of analyte test strips may be disposed on the second supporting surface. It should be appreciated that the interior side of the base may include more than two supporting surfaces.

Each supporting surface may have a specific shape—e.g., circular or semi-circular shaped, elliptical or semi-elliptical shaped, ring-shaped, square or rectangular shaped, other polygonal shape, or other regular or irregular shape. The supporting surface may also be shaped as part of one of the above shapes. For example, a supporting surface may be partially circular or elliptical—e.g., shaped as a third of a circle or ellipse, a quarter of a circle (ellipse), etc.

Each supporting surface may be a specific type—e.g., planar or non-planar. The term "planar" is used herein to mean a flat surface that falls within a plane. The term "non-planar" is used herein to mean a surface that does not fall within—e.g., convex, concave, other curved shape surface, etc.

Furthermore, each supporting surface may have a certain orientation—e.g., level, angled, etc. The term "level" or "level surface" is used herein to refer to a surface that is horizontal or orthogonal to the longitudinal axis of the container. The term "angled" or "angled surface" is used herein to refer to a surface that is not level or orthogonal to the longitudinal axis. The degree of the angle is measured with respect to the latitudinal axis that is perpendicular to the longitudinal axis. Thus, a surface angled at a smaller degree than another surface is closer to being level than the other surface.

For example, two or more supporting surfaces may be planar and level. In other instances, two or more supporting surfaces may be planar and angled. In other instances, one supporting surface may be planar and level while another supporting surface may be planar and angled. It should be appreciated that the shapes, types, and orientations are referred to herein generally and are not required to be exact, but rather substantially or approximately the shape, type, or orientation stated. For example, when a surface is said to be circular shaped, this includes surfaces that are substantially or approximately circular shaped.

It should be appreciated that various combinations of shapes, types, and orientations of supporting surfaces may be implemented—e.g., on the interior side of the base of a container, and/or on the interior side of an insert (described in further detail later). Various embodiments described herein and shown in the figures are exemplary and should not be taken as limiting the scope of the present disclosure.

In certain embodiments, one supporting surface may be longitudinally offset from one or more other supporting surfaces. The term "longitudinally offset" and "longitudinal offset" are used herein to refer to a space or gap in longitudinal height between adjacent supporting surfaces. Because of the longitudinal offset, analyte test strips disposed on a first supporting surface next to the second supporting surface are at a sufficiently different height than the analyte test strips disposed on the second supporting surface next to the first supporting surface. This exposes enough of the sides of the higher analyte test strips to permit a user to grip an analyte test strip.

For example, the first supporting surface may be raised relative to the second supporting surface in the longitudinal direction. For example, the first supporting surface may extend, project, protrude, etc., closer towards the distal end of the container than the second supporting surface, thus disposing analyte test strips at a higher height than the second supporting surface. The difference in height between the higher analyte test strips and the lower analyte test strips creates a region of space above the lower analyte test strips and adjacent to the higher analyte test strips. This region of space exposes the sides of the distal ends of the higher analyte test strips that are next to the lower analyte test strips, thus enabling the user to position a finger tip along the side of a higher analyte test strip and sufficiently grip the test strip to displace it away from the rest of the analyte test strips. This region of space is also referred to herein generally as the "offset region". Moreover, when the number of analyte test strips in the container have been reduced, one or more analyte test strips may be brought to the higher first supporting surface—e.g., by gently shaking the container.

The length of the longitudinal offset may vary but should be large enough to enable a finger tip to sufficiently grip enough of the side of a higher analyte test strip to enable the user to pull the analyte test strip away from the other analyte test strips and toward the opening of the container. Example lengths of the longitudinal offset may range from, for example, 2 mm or more, such as 4 mm or more, and including 8 mm or more. In some embodiments, the longitudinal offset is between 2 mm and 10 mm, such as between 4 mm and 8 mm. The maximum of the longitudinal offset depends on the longitudinal length of the cavity and the analyte test strips. The longitudinal offset should not be so large as to make the higher analyte test strips extend out of the opening of the container and prevent the container from being closed. For example, if the analyte test strip container is 5 cm long and the analyte test strips are 3 cm long, then the maximum longitudinal offset is 2 cm.

The width of the offset region may vary but should be large enough to enable a finger tip to be inserted alongside the higher analyte test strips without be obstructed by the lower analyte test strips. In this way, the user may sufficiently displace the analyte test strip from the other analyte test strips to "grab" it—e.g., by pinching the analyte test strip between the thumb and the finger used to displace it. It should be appreciated that in some instances, friction between the user's finger and the side of the analyte test strip in the offset region may assist the user in pulling the test strip toward the opening, thus requiring minimal force applied by the user into the analyte tests strip. Example widths of the offset region at a middle height in the offset region may range from, for example, 4 mm or more, such as 8 mm or more, including 10 mm or more.

It should be appreciated that any variety of combinations of types, orientations, and shapes of supporting surfaces on the interior side of the base of a container may be longitudinally offset without compromising the underlying principles of the present disclosure. Various embodiments described herein and shown in the figures are exemplary and should not be taken as limiting the scope of the present disclosure.

For example, in certain embodiments, each supporting surface may be planar and level, with adjacent supporting surfaces longitudinally offset from one another. For example, a cylindrical container may include a planar and level first supporting surface that is circularly shaped and that is raised with respect to a planar and level second supporting surface located concentrically around the first supporting surface in a ring shape.

In some instances, the base of the container may include an exterior that is entirely planar and level. In such cases, the interior side of the base may be formed in a manner, for example, to include the appropriate contours for the supporting surfaces, while the exterior of the base remains planar and level.

In some instances, the base of the container may include an exterior that is indented or recessed longitudinally in towards the inside of the container (e.g., in areas that correspond to the supporting surfaces that are raised or longitudinally higher on the interior side of the base). In such cases, the entire base may, for example, be pressed, stamped, molded, or otherwise formed to include the appropriate contours to form the supporting surfaces.

It should be appreciate that the containers may be made from any variety of materials that provide the analyte test strips with protection from contamination, such as dirt, oil, debris, water vapor and moisture, etc. For example, containers may be made from metals, metal alloys, polymers (e.g., hard plastics), or any other suitable material or combination of materials. For instance, the container may be made out of polypropylene and then lined with a desiccant material to absorb water vapor. In some instances, the housing may be made from a material that acts as a strong barrier to water vapor and moisture—e.g., cycloolefin copolymer, etc.

In some embodiments, a cap is provided to close the container and provide a sealed environment for the analyte test strips. The cap may provide protection from dirt, oils, debris, water vapor and moisture, and/or other contaminants. The cap may be made out a variety of materials—e.g., metals, metal alloys, polymers (e.g., plastics), etc.

It should also be appreciated that the containers may include a desiccant to absorb moisture within the container. Desiccant may be implemented in a variety of manners—e.g., loose desiccant powder encased in a secondary container; extruded to form a film or solid block; co-molded with a polymer to make a solid plastic block that has desiccating properties, etc. In certain embodiments, the desiccant may line the interior surface of the sidewalls, cap, and/or interior side of the base. In some instances, one or more supporting surfaces may include a desiccant layer.

Figure 4A:
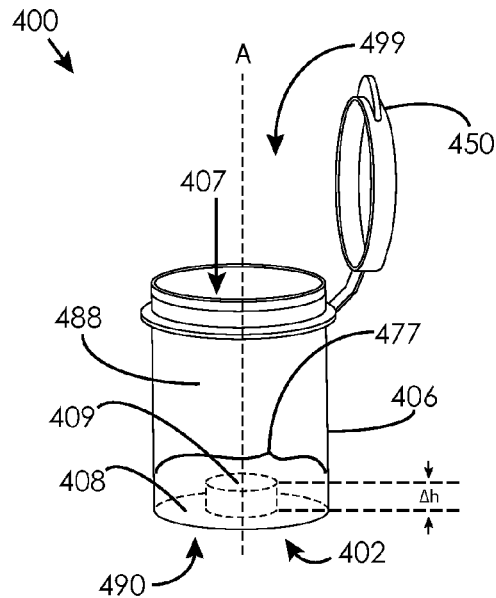
FIG. 4A illustrates a perspective view of a container, according to certain embodiments.

FIG. 4A illustrates a perspective view of a container, according to certain embodiments in the present disclosure. Container 400 is shown having a base 402 at proximal end 490, sidewall 406 extending from the base 402 and forming a cavity 488 in the container 400 with an opening 407 at a distal end 499. Container 400 is also shown comprising a cap 450 that closes the container 400 and may provide a sealed environment for the analyte test strips disposed therein.

An interior side 477 of the base 402 is shown varying in height with respect to longitudinal axis A, which extends through the opening 407 and the base 402 of the container 400. The interior side 477 of base 402 forms the cavity floor and is comprised of a first supporting surface 408 and a second supporting surface 409 that each support a respective plurality of analyte test strips when disposed in the container 400. The term "cavity floor" is used herein to refer generally to the one or more surfaces at the proximal end of the cavity that the analyte test strips are disposed on. Supporting surface 409 is at a higher longitudinal height in the container 400 than supporting surface 408—longitudinally offset by a distance Δh.

Supporting surface 409 is planar and level. Supporting surface 409 comprises a raised circular surface that is projects concentrically in the circular contour of the base 402 of the container 400. Supporting surface 408 is also planar and level. Supporting surface 408 is comprised of the unraised surface of the base 402 located concentrically around the outside of the first supporting surface 409. Supporting surface 408 is a ring shaped surface around the first supporting surface 409.

Figure 4B:
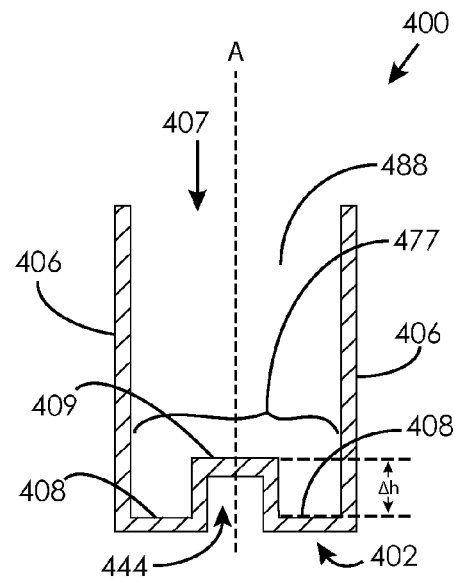
FIG. 4B illustrates a partial cross-sectional view of the analyte test strip container shown in FIG. 4A, according to certain embodiments.

FIG. 4B illustrates a partial cross-sectional view of the analyte test strip container shown in FIG. 4A, according to certain embodiments. Container 400 is shown including opening 407, sidewall 406, cavity 488, and base 402. The interior side 477 of the base 402 includes supporting surface 409 and supporting surface 408 at different heights along the longitudinal axis A which extends through the base 402 and opening 407 the container 400.

Figure 4C:
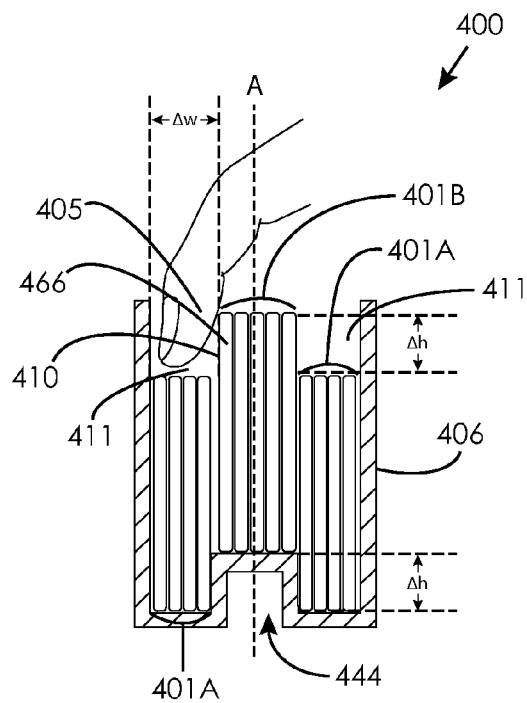
FIG. 4C illustrates a partial cross-sectional view of the analyte test strip container shown in FIG. 4A when full of analyte tests trips, according to certain embodiments.
Figure 4D:
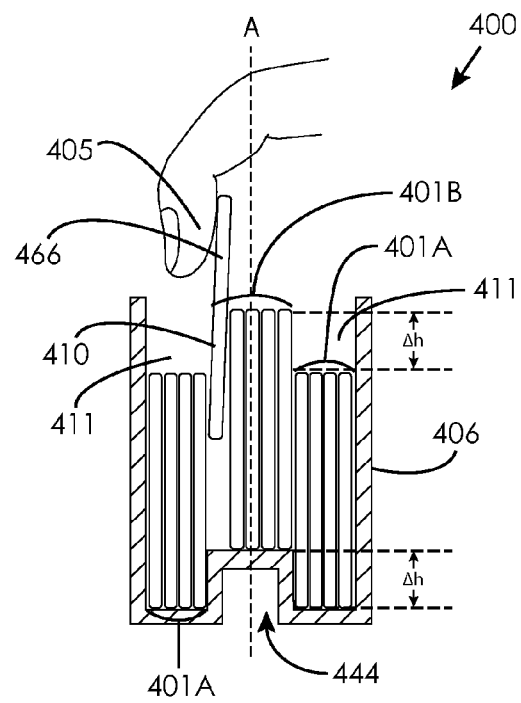
FIG. 4D illustrates a partial cross-sectional view of the analyte test strip container shown in FIG. 4A as a user grips and pulls the selected analyte test strip away from the remaining analyte test strips.

FIG. 4C illustrates a partial cross-sectional view of the analyte test strip container shown in FIG. 4A when full of analyte tests trips, according to certain embodiments. The analyte test strips 401B that are disposed on the supporting surface 409 are disposed higher within the cavity 477 of the container 400 than the analyte test strips 401A that are disposed on the supporting surface 408. The difference in height Δh between analyte test strips 401A and 401B corresponds with the longitudinal offset height Δh between the supporting surface 408 and supporting surface 409. The difference in height Δh between the analyte test strips 401A and 401B creates offset region 411 next to the distal ends of the analyte test strips 401B that are disposed adjacent to and higher than the analyte test strips 401A. This enables the user to insert a finger 405 into the offset region 411 to grip a side 410 of the distal end of an analyte test strip (e.g., selected test strip 466) that is on supporting surface 409 and adjacent to the offset region 411. The user may then pull the selected analyte test strip 466 away from analyte test strips 401B and out the opening 407 of the container 400, as illustrated in FIG. 4D. Moreover, it is also noted that when the number of analyte test strips in the container have been reduced, one or more analyte test strips may be brought from the lower supporting surface 408 to the higher supporting surface 409—e.g., by gently shaking the container.

The offset region 411 is shown having a width Δw. As stated before, the width Δw may vary but should be wide enough to permit a user's finger to be inserted alongside the analyte test strips that are adjacent to offset region 411. Furthermore, as stated before, the height of the offset region 411 and longitudinal offset height Δh may vary in size but should be large enough to expose a sufficient amount of the side 410 of the distal end of the analyte test strips that are adjacent to offset region 411 to permit the user's finger 405 to sufficiently grip the side 410 a selected analyte test strip 466.

The offset region 411 enables the user to apply force against the side 410 of the selected analyte test strip 466 as well as towards the opening 407 of the container 400 to displace the analyte test strip 466 away from the analyte test strips 401B. In this way, the user may sufficiently displace the analyte test strip 466 from the analyte test strips 401B to grab it—e.g., by pinching the analyte test strip 466 between the thumb and finger 405 used to displace the test strip 466. It should be appreciated that in some instances, friction between the user's finger 405 and the side 410 of the analyte test strip 466 in the offset region 411 region may assist the user in pulling the test strip toward the opening 407, thus requiring minimal force applied by the user's finger 405 into the analyte tests strip 466.

It should also be noted that in FIGS. 4B, 4C, and 4D, the exterior of base 402 is shown to include a recess or indentation 444. The recess 444 is circularly shaped and corresponds with the formation of the raised surface 409. Furthermore, the recess 444 is positioned in the center of the base 402 that is otherwise planar and level. The positioning of the recess 444 in the center of the base 402 permits the container 400 to remain standing in a stable manner. Stamping, pressing, molding, or otherwise forming the base of the container with a recess may provide a convenient way to form the supporting surfaces and yet maintain stability for the container. It should be appreciated that the size, shape, and positioning of the recess may be varied in other embodiments, and still maintain stability. Furthermore, it should be appreciated that in other embodiments, the exterior side of the base 402 may be entirely planar and level across the base 402 even though the interior side of the base 402 has a varying height (e.g., has different height supporting surfaces).

Additional embodiments are shown below. It should be appreciated that the following embodiments are exemplary and the underlying principles of the present disclosure are not limited to the illustrated embodiments. Furthermore, for the sake of brevity, some repetitive features are not identified or described again, but may still apply.

FIGS. 5A and 5B illustrate a perspective and a partial cross-sectional view of a container, respectively, according to certain embodiments. Container 400 is shown having a base 402 at proximal end 490, sidewall 406 extending from the base 402 and forming a cavity 488 in the container 400 with an opening 407 at a distal end 499. Container 400 is also shown comprising a cap 450 that closes the container 400 and may provide a sealed environment for the analyte test strips disposed therein.

An interior side 477 of the base 402 is shown varying in height with respect to longitudinal axis A, which extends through the opening 407 and the base 402 of the container 400. The interior side 477 of base 402 forms the cavity floor and is comprised of a first supporting surface 408 and a second supporting surface 409 that each support a respective plurality of analyte test strips when disposed in the container 400. Supporting surface 409 is at a higher longitudinal height in the container 400 than supporting surface 408; and further, is longitudinally offset by a distance $\Delta h$. In this embodiment, the exterior side of the base 402 is shown planar and level as opposed to recessed.

Supporting surface 408 and supporting surface 409 are longitudinally offset from one another, and are each planar and level. Supporting surface 409 is a raised semi-circular shaped surface that is longitudinally offset a distance of $\Delta h$ from supporting surface 408, which also has a semi-circular shape. The analyte test strip 401A on supporting surface 408 are disposed in the container 400 at a lower height than the analyte test strips 401B on the supporting surface 409. The offset region 411 formed by the longitudinal offset exposes a side 410 of some of the higher analyte test strips 401B that are adjacent to the offset region 411. Accordingly, the user may grip the side 410 of an exposed test strip 466 and pull it away from the analyte test strips 401B.

FIGS. 6A and 6B illustrate a perspective and a partial cross-sectional view of a container, respectively, according to certain embodiments. Container 400 is shown having a base 402 at proximal end 490, sidewall 406 extending from the base 402 and forming a cavity 488 in the container 400 with an opening 407 at a distal end 499. Container 400 is also shown comprising a cap 450 that closes the container 400 and may provide a sealed environment for the analyte test strips disposed therein.

An interior side 477 of the base 402 is shown varying in height with respect to longitudinal axis A, which extends through the opening 407 and the base 402 of the container 400. The interior side 477 of base 402 forms the cavity floor and is comprised of a supporting surface 408A, a supporting surface 408B, and supporting surface 409 that each support a respective plurality of analyte test strips when disposed in the container 400. Supporting surface 409 is at a higher longitudinal height in the container 400 than supporting surfaces 408A and 408B—longitudinally offset by a distance $\Delta h$. The exterior of the base 402 includes recesses 444 that correspond with the raised surface 409. The ring-shaped recess 444 on the exterior of the planar and level base 402 does not inhibit the container 400 from remaining standing and stable.

Supporting surface 408A, a supporting surface 408B, and supporting surface 409 are each planar and level. Supporting surface 409 is a raised ring shaped surface that is longitudinally offset a distance of $\Delta h$ from supporting surfaces 408A and 408B. Supporting surface 408A is a surface of the base 402 located concentrically around the outside of the ring shaped supporting surface 409. Further, supporting surface 408B is a surface of the base 402 located concentrically within the ring shaped supporting surface 409.

The analyte test strips 401A on supporting surfaces 408A and 408B are disposed in the container 400 at a lower height than the analyte test strips 401B on the supporting surface 409. The offset regions 411 are formed by the longitudinal offsets and expose sides 410 of some of the higher analyte test strips 401B that are adjacent to the offset regions 411. Accordingly, the user may grip the side 410 of an exposed test strip and pull it away from the analyte test strips 401B. It should be appreciated that in certain embodiments one offset region may be different shaped or sized from another offset region.

Figure 7A:
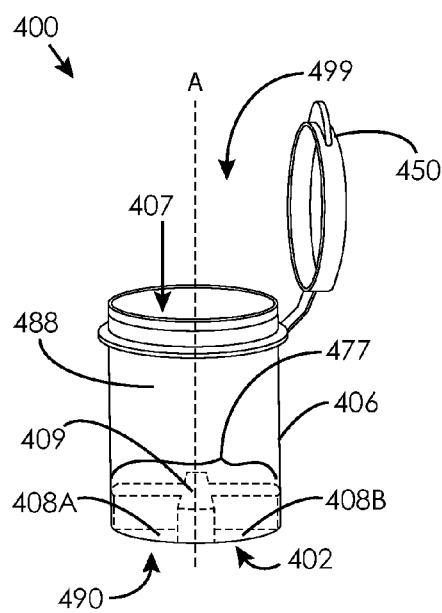
FIGS. 7A and 7B illustrate a perspective and a partial cross-sectional view of a container, respectively, according to certain embodiments.
Figure 7B:
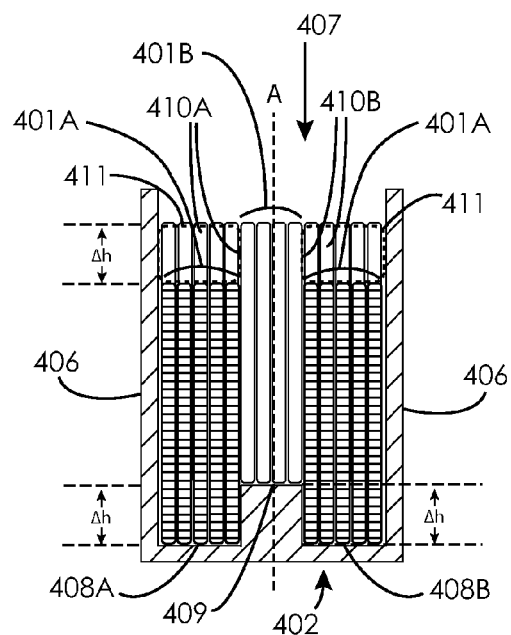

FIGS. 7A and 7B illustrate a perspective and a partial cross-sectional view of a container, respectively, according to certain embodiments. Container 400 is shown having a base 402 at proximal end 490, sidewall 406 extending from the base 402 and forming a cavity 488 in the container 400 with an opening 407 at a distal end 499. Container 400 is also shown comprising a cap 450 that closes the container 400 and may provide a sealed environment for the analyte test strips disposed therein.

An interior side 477 of the base 402 is shown varying in height with respect to longitudinal axis A, which extends through the opening 407 and the base 402 of the container 400. The interior side 477 of base 402 forms the cavity floor and is comprised of a supporting surface 408A, supporting surface 408B, supporting surface 408C (not shown), supporting surface 408D (not shown), and supporting surface 409 that each support a respective plurality of analyte test strips when disposed in the container 400. Supporting surface 409 is at a different longitudinal height in the container 400 than supporting surfaces 408A, 408B, 408C, and 408D—longitudinally offset by a distance $\Delta h$.

Supporting surfaces 408A, 408B, 408C, and 408D, as well as supporting surface 409, are each planar and level. Supporting surface 409 is a raised cross shaped surface that is longitudinally offset a distance of $\Delta h$ from supporting surfaces 408A, 408B, 408C, and 408D. The raised surface is shown as two rectangular raised strips crossing one another and delineating four quadrants of the supporting surfaces 408A, 408B, 408C, and 408D, respectively. The analyte test strips 401A on the supporting surfaces 408A, 408B, 408C, and 408D are disposed in the container 400 at a different height than the analyte test strips 401B on the supporting surface 409. It is noted that in FIG. 7B, analyte test strips 401A are illustrated with vertically hatched lines and are shown for only two supporting surface 408A and 408B since the other two supporting surfaces 408C and 408D are not shown.

The analyte test strips 401A on supporting surfaces 408A, 408B, 408C, and 408D are disposed in the container 400 at a lower height than the analyte test strips 401B on the supporting surface 409. The offset regions 411 (approximately illustrated by dotted lines) are formed by the longitudinal offsets and expose sides 410 of some of the higher analyte test strips 401B that are adjacent to the offset regions 411. Accordingly, the user may grip the side 410 of an exposed test strip and pull it away from the analyte test strips 401B. It should be appreciated that in certain embodiments one offset region may be different shaped or sized from another offset region.

Figure 8A:
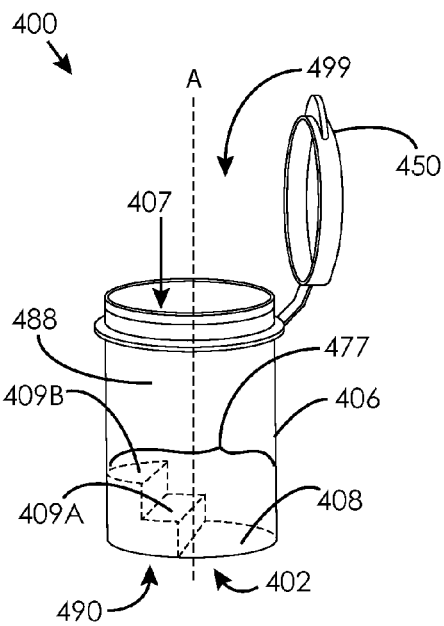
FIGS. 8A and 8B illustrate a perspective and a partial cross-sectional view of a container, respectively, according to certain embodiments.
Figure 8B:
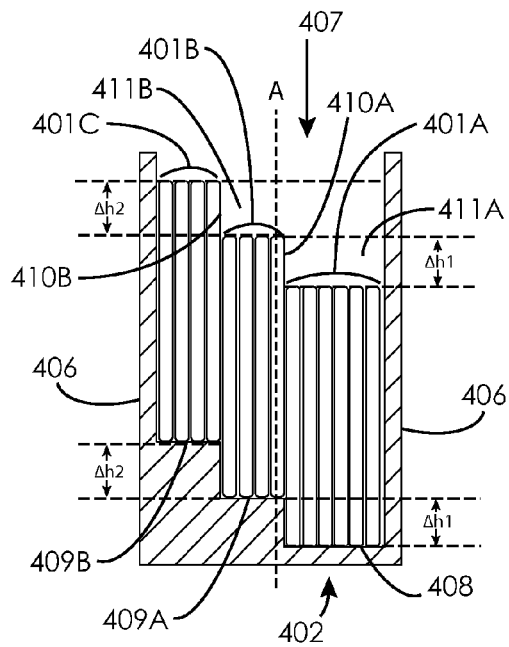

FIGS. 8A and 8B illustrate a perspective and a partial cross-sectional view of a container, respectively, according to certain embodiments. Container 400 is shown having a base 402 at proximal end 490, sidewall 406 extending from the base 402 and forming a cavity 488 in the container 400 with an opening 407 at a distal end 499. Container 400 is also shown comprising a cap 450 that closes the container 400 and may provide a sealed environment for the analyte test strips disposed therein.

An interior side 477 of the base 402 is shown varying in height with respect to longitudinal axis A, which extends through the opening 407 and the base 402 of the container 400. The interior side 477 of base 402 forms the cavity floor and is comprised of a supporting surface 408, supporting surface 409A, and supporting surface 409B that each support a respective plurality of analyte test strips when disposed in the container 400. Supporting surface 409A is at a higher longitudinal height in the container 400 than supporting surface 408—longitudinally offset by a distance $\Delta h1$. Further, supporting surface 409B is at a higher longitudinal height in the container 400 than supporting surface 409A—longitudinally offset by a distance $\Delta h2$.

Supporting surfaces 408, 409A, and 409B are each planar and level. Supporting surfaces 409A and 409B form raised step-like surfaces that increment in height to provide longitudinal offsets $\Delta h1$ and $\Delta h2$. The analyte test strips 401A on supporting surface 408 are disposed in the container 400 at a lower height than the analyte test strips 401B on the supporting surface 409A. The offset region 411A is formed by the longitudinal offset $\Delta h1$ and exposes a side 410A of some of the higher analyte test strips 401B that are adjacent to the offset region 411A. Accordingly, the user may grip the side 410A of an exposed test strip and pull it away from the analyte test strips 401B.

Furthermore, the analyte test strips 401B on supporting surface 409A are disposed in the container 400 at a lower height than the analyte test strips 401C on the supporting surface 409B. The offset region 411B is formed by the longitudinal offset $\Delta h2$ and exposes a side 410B of some of the higher analyte test strips 401C that are adjacent to the offset region 411B. Accordingly, the user may grip the side 410B of an exposed test strip and pull it away from the analyte test strips 401C. It should be appreciated that additional supporting surfaces may be implemented in other embodiments.

Figure 9A:
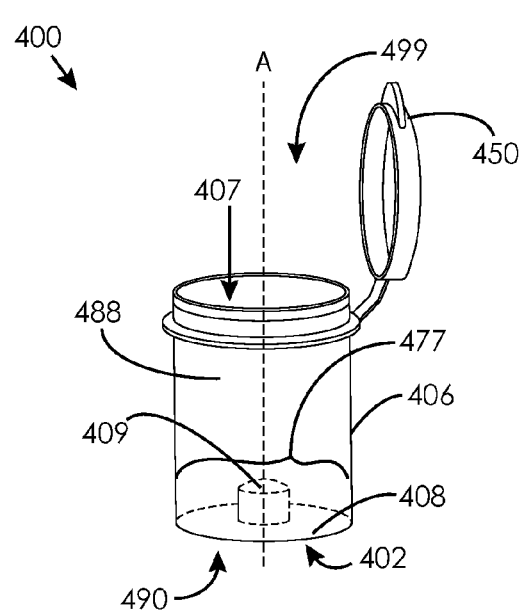
FIGS. 9A and 9B illustrate a perspective and a partial cross-sectional view of a container, respectively, according to certain embodiments.
Figure 9B:
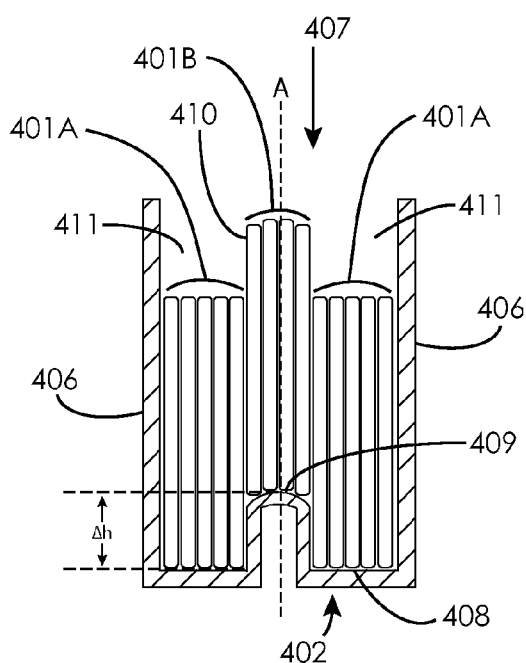

FIGS. 9A and 9B illustrate a perspective and a partial cross-sectional view of a container, respectively, according to certain embodiments. Container 400 is shown having a base 402 at proximal end 490, sidewall 406 extending from the base 402 and forming a cavity 488 in the container 400 with an opening 407 at a distal end 499. Container 400 is also shown comprising a cap 450 that closes the container 400 and may provide a sealed environment for the analyte test strips disposed therein.

An interior side 477 of the base 402 is shown varying in height with respect to longitudinal axis A, which extends through the opening 407 and the base 402 of the container 400. The interior side 477 of base 402 forms the cavity floor and is comprised of a first supporting surface 408 and a second supporting surface 409 that each support a respective plurality of analyte test strips when disposed in the container 400. Supporting surface 409 is at a higher longitudinal height in the container 400 than supporting surface 408; and further, is longitudinally offset by a distance $\Delta h$.

Supporting surface 408 is planar and level, and supporting surface 409 is a curved surface that is projected to a higher height. Supporting surface 409 comprises a raised circular and convex surface located concentrically in the circular contour of the base 402 of the container 400. Supporting surface 408 is comprised of the unraised surface of the base 402 located concentrically around the outside of the first supporting surface 409. Supporting surface 408 is a ring shaped surface around the first supporting surface 409.

The analyte test strips 401B that are disposed on the supporting surface 409 are disposed higher within the cavity 477 of the container 400 than the analyte test strips 401A that are disposed on the supporting surface 408. The difference in height $\Delta h$ between analyte test strips 401A and 401B corresponds with the longitudinal offset height $\Delta h$ between the supporting surface 408 and supporting surface 409. The difference in height $\Delta h$ between the analyte test strips 401A and 401B creates an offset region 411 next to the distal ends of some of the analyte test strips 401B that are disposed adjacent to and higher than the analyte test strips 401A.

It should be appreciated that the embodiments shown in the figures are exemplary, and that other shapes, types, and orientations may be implemented in other embodiments. For example, while most surfaces were shown to be planar and level, it should be appreciated that in other embodiments, one or more of the supporting surfaces may be non-planar or angled. Furthermore, it should also be appreciated that the raised surfaces may vary in position on the interior side of the base in other embodiments.

In some aspects of the present disclosure, inserts are provided. The inserts are sized to fit within an opening of an analyte test strip container and situate in the cavity of the container. The inserts are sized and shaped to fit within a cavity of an analyte test strip container and to situate within the cavity. The inserts are situated in the cavity so as to create a cavity floor that varies in height with respect to a longitudinal axis of the container. Similarly as described above, the varying height of the cavity floor enables the test strips to be disposed in the container with a space created next to analyte test strips so as to expose the sides of the distal ends of some analyte test strips, making it easier for the user to grip and displace a test strip from the container.

The analyte test strip containers in which the inserts situate are analyte test strip containers with generally planar and level bases, with cavity floors that do not vary in height with respect to the longitudinal axis of the container (e.g., analyte test strip containers in the prior art embodiments described above for FIGS. 1-3). Example analyte test strip containers in which the inserts situate may be found in U.S. Pat. Nos. 5,723,085 and 5,911,937, the disclosures of which are both incorporated by reference herein.

Thus, without the inserts, the analyte test strip containers store all of the analyte test strips in the container at approximately the same height longitudinally. The distal ends of the test strips act collectively as a sort of barrier or surface that prevents the user from easily gripping or grabbing a test strip. It should be appreciated that the inserts may be used with any variety of containers where the test strips are approximately the same height or otherwise positioned in a manner that makes them difficult to grab when generally full. It should also be appreciated that the inserts may be situated in a container with any variety of shaped bases as long as the insert is able to situate within the cavity either above the base or against the base of the container. While the proximal end of the insert is shown in some embodiments to fit flushly against the interior side of the base, it should be appreciated that the proximal end of the insert does not have to be shaped to fit flushly against the interior side of the base or have a shape that mates with the interior side of the base. In some instances, the proximal end of the insert may not necessarily abut the interior side of the base when situated within the container—e.g., it may situate near the base with a gap or space between the base and insert.

The inserts include a proximal side that faces the base of the container when inserted into the container. The inserts also include an interior side which faces the opening of the cavity when situated within the cavity. When situated within the cavity of the container, the insert provides for a cavity floor with a varying height with respect to a longitudinal axis extending through the base and the opening of the container.

The cavity floor supports the analyte test strips on supporting surfaces and comprises the interior side of the insert. In certain embodiments, the interior side of the insert forms all of the cavity floor. In other embodiments, the cavity floor also comprises part of the interior side of the base—e.g., the insert does not cover the entire interior side of the base.

In some instances, the insert is sized to fit within the cavity such that it may move around. In other instances, the insert is shaped and sized to fit within the cavity such that it is generally fixed. For example, the insert may be shaped similar to the base of the container and sized to be slightly smaller than the opening of the container so that it may be inserted within the cavity yet be snug enough to remain generally fixed. It should be appreciated that degree of "snugness" of the insert when situated within the container may vary depending on the size and shape of the insert with respect to the cavity. For example, the closer the contour of the cavity is in size to the contour of cavity of the container, the more stable the insert will be inside the container and the more apt the insert will be to situated in a generally fixed position within the container. A snug fit may be achieved if the contour of the insert is so close in size to the contour of the container that the two slightly contact one another, providing friction when inserting the insert into the container. It should be appreciated that if the contour of the insert is too large, the insert will not fit in the cavity or too much force will be required to insert the insert into the cavity. It should also be appreciated that as the insert becomes smaller in size relative to the cavity, the insert is more easily inserted without touching the container, but also less stable and apt to move around within the container instead of remaining in a generally fixed position.

It should also be appreciated that the insert does not have to cover the entire base of the container to be generally fixed. For example, the insert may be sized to be half the size of the base—e.g., a semi-circular or semi-elliptical insert that is slightly smaller than a circular or elliptical base—or even greater than half the size and shape of the base. Or, as another example, the insert may be cross shaped and sized to span to the perimeter of the base (e.g., circular base, square base, etc.). In such cases, the insert may still be shaped and sized to remain relatively fixed within the container. Furthermore, as stated above, the insert may be situated within the cavity either above the base or against the base of the container in different embodiments. For example, if the base of the container is a planar circular surface, then the proximal side of the insert may include a corresponding planar circular surface that is sized to fit against the base of the container.

It should also be appreciated that the inserts may be made from any variety of materials. For example, inserts may be made from metals, metal alloys, polymers (e.g., hard plastics), or any other suitable material or combination of materials.

In certain embodiments, the inserts may include a desiccant to absorb moisture within the container. Example methods of implementing desiccant with the insert may include encasing the loose desiccant powder within the insert; forming a film or layer of desiccant on the insert; co-molding desiccant with the material (e.g., polymer) used to make the insert; etc. It should also be appreciated that additional desiccant may be included within the container—e.g., line the interior surface of the sidewalls, cap, and/or interior side of the base.

In certain embodiments, the insert comprises a securing member that has a contour shaped and sized to be slightly smaller than the contour of the opening of the container such that the insert may be inserted within the opening and situate with the desired level of snugness. For example, in some instances, the securing member may be disc shaped member and sized slightly smaller than the circular opening of the container. In some instances, the securing member may be positioned at the proximal end of the insert such that a proximal surface of the securing member is adjacent to or abutting the interior side of the base of the container when situated.

The insert further comprises a distal side of the insert (also referred to herein as the interior side of the insert) that includes one or more protrusions extending from the securing member. One or more supporting surfaces may be provided at a distal end of the protrusions for supporting analyte test strips disposed thereon. Furthermore, one or more supporting surfaces may be provided by the distal side of the securing member.

Figure 10A:
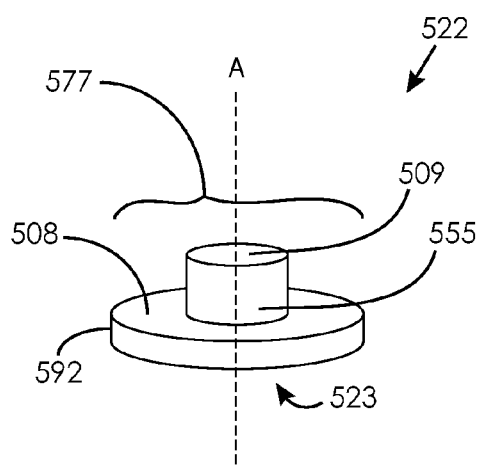
FIG. 10A illustrates a perspective view of an insert, according to some embodiments.
Figure 10B:
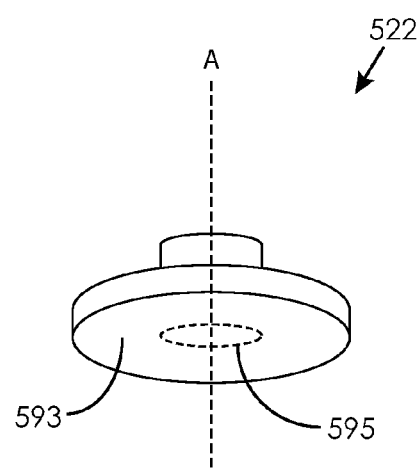
FIG. 10B illustrates a perspective view of the bottom of the insert shown in FIG. 10A, according to some embodiments.

FIG. 10A illustrates a perspective view of an insert, according to some embodiments. FIG. 10B illustrates a perspective view of the bottom of the insert shown in FIG. 10A, according to some embodiments. Insert 522 is shown comprising a securing member 592 that is disc shaped and positioned at the proximal end 523 of the insert 522. Securing member 592 has a circular contour sized to be slightly smaller than the circular contour of the opening of a cylindrical container (e.g., a vial) such that the insert 522 may be inserted within the opening of the container and situate with the desired level of snugness. Protrusion 555 is shown to be cylindrical shaped and extends from a distal side of the securing member 592 and includes a surface 509 at a distal end of the protrusion 555. The interior side 577 of the insert 522 includes a supporting surface 508 provided by the distal side of the securing member 592, and supporting surface 509 provided by the surface at the distal end of the protrusion 555. Supporting surface 509 is shown as a raised with respect to supporting surface 508 along longitudinal axis A. As shown in FIG. 10B, securing member 592 includes a proximal surface 593 that is adjacent to or abutting the interior side of the base of the container when situated within the container. In the embodiment shown, the proximal surface 593 of the securing member is planar and level and may reside flushly against the interior side of the base of a container. In some embodiments, the proximal surface 593 may include a recess or indentation (as represented by dotted line 595) that corresponds with the formation of the protrusion 555.

In use, user may hold the insert by the protrusion 555, for example, and insert the proximal end 523 of the insert 522 into the opening of a container such that the securing member is properly aligned within the opening and cavity of the container. The user may continue to hold the protrusion 55 and use it to push the insert 522 completely into the container until the proximal side 593 of the insert 522 abuts the base of the container. The insert 522 is then maintained within the container such that the interior side 577 of the insert 522 faces the opening of the container and provides a cavity floor with a varying height—e.g., a first supporting surface provided by the distal side of the securing member, and a second supporting surface 509 provided by the distal surface of the protrusion 555.

It should be appreciated that in other embodiments, the securing member may not necessarily abut the base of the container. It should also be appreciated that the protrusion and securing member may be any variety of shapes and sizes. The securing member, and equivalents thereof, serve to securely fit within the contour of the container to enable the insert to remain in a generally fixed position when situated within the container.

In some aspects of the present disclosure, analyte test strip container systems are provided. The analyte test strip container systems comprise, for example, a container for storing a plurality of analyte test strips and an insert sized to fit within the container. The container includes a base, one or more sidewalls extending from the base, and a cavity having an opening at a distal end and the base at the proximal end. As will be fully explained below, inserts, and equivalents thereof, serve as means for providing a cavity floor with a varying height with respect to a longitudinal axis. The insert is sized to fit within the opening of the cavity and to situate within the cavity to provide the cavity floor with a varying height with respect to a longitudinal axis extending through the base and the opening of the container. The cavity floor may comprise, for example, one or more supporting surfaces that support analyte test strips disposed thereon.

The cavity floor comprises an interior side of the insert. The term "interior side of the insert" is used herein to refer generally to the distal side of the insert that faces the opening of the cavity. The interior side of the insert may include one or more supporting surfaces that support analyte test strips disposed thereon. As stated above, in certain embodiments, the interior side of the insert forms all of the cavity floor. In other embodiments, the cavity floor comprises the interior side of the insert and a portion of the interior side of the base that is not covered by the insert.

As mentioned above, it should be appreciated that various combinations of shapes, types, and orientations of supporting surfaces may be implemented. For the sake of clarity and brevity, example shapes, types, and orientations, and combinations thereof, will not be described in detail again, but rather reference is made to the previous discussion of these features. Furthermore, it should be appreciated that similar concepts and features of the analyte test strip containers described above for FIGS. 1-9 may also apply to the sections for inserts, analyte test strip systems, methods of manufacturing analyte test strip containers, and methods of adapting analyte test strip containers. For example, the example ranges of lengths of longitudinal offsets between supporting surfaces, as well as the example ranges of widths of offset regions, discussed previously will also apply to the sections on inserts, analyte test strip systems, methods of manufacturing analyte test strip containers, and methods of adapting analyte test strip containers. For the sake of brevity, some similar concepts and features are not repeated but may still apply to the other sections.

In certain embodiments, the cavity floor may include more than one supporting surface. For example, the cavity floor may comprise a first supporting surface that supports a first plurality of analyte test strips thereon, and a second supporting surface that supports a second plurality of analyte test strips thereon. It should be appreciated that the cavity floor may also include three, four, or any other number of additional supporting surfaces. It should also be appreciated that in embodiments where the interior side of the insert forms all of the cavity floor, the interior side of the insert may include two or more supporting surfaces that support respective plurality of analyte test strips.

In certain embodiments, the cavity floor comprises an interior side of the base in addition to the interior surface of the insert. For example, the insert may not cover the entire base of the container when situated within the cavity. In such case, the uncovered portion of the base may provide one or more supporting surfaces in which analyte test strips may be disposed. For example, in some instances, the cavity floor may comprise two supporting surfaces: one supporting surface provided by the insert and another supporting surface provided by the base.

It should be appreciated that the interior surface of the insert and the interior side of the base may each include one or more supporting surfaces. In some instances, for example, the base may provide one supporting surface and the insert provide two or more supporting surfaces. In some instances, for example, the insert may divide the base up into two or more supporting surfaces with the insert providing one or more additional supporting surfaces itself.

In certain embodiments, the cavity floor comprises two or more supporting surfaces that are longitudinally offset—e.g., a supporting surface on the interior side of the base longitudinally offset from a supporting surface on the interior side of the insert; and/or one supporting surface on the interior side of the insert that is longitudinally offset from another supporting surface on the interior side of the insert; etc.

It should be appreciated that any variety of combinations of types, orientations, and shapes of supporting surfaces on the cavity floor may be longitudinally offset without compromising the underlying principles of the present disclosure. For the sake of clarity and brevity, example shapes, types, orientations, and combinations thereof, for supporting surfaces, will not be described in detail again, but rather reference is made to the previous discussion of these features.

In certain embodiments, the cavity floor may comprise the interior side of the insert and not the interior side of the base. For example, the insert may cover the entire base of the container with the interior side of the insert forming all of the cavity floor. In such case, the interior side of the insert includes all of the one or more supporting surfaces in which analyte test strips may be disposed.

In certain embodiments, the cavity floor comprises two or more supporting surfaces that are longitudinally offset. For example, one supporting surface on the interior side of the insert may be longitudinally offset from another supporting surface on the interior side of the insert. It should be appreciated that additional supporting surfaces (e.g., a third supporting surface, etc.) may also be included on the on the interior side of the insert and may be longitudinally offset from one or more other supporting surfaces.

Figure 11A:
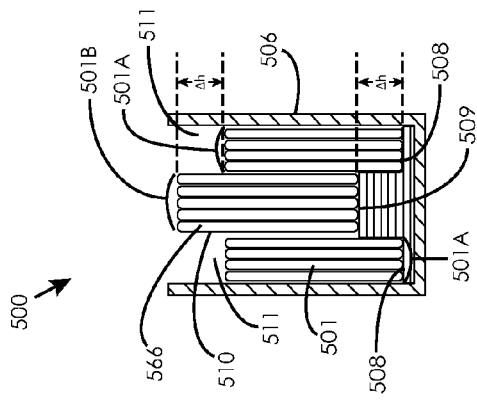
FIG. 11A illustrates a perspective view of an analyte test strip container and insert before the insert is situated within the cavity of the container, according to certain embodiments.
Figure 11B:
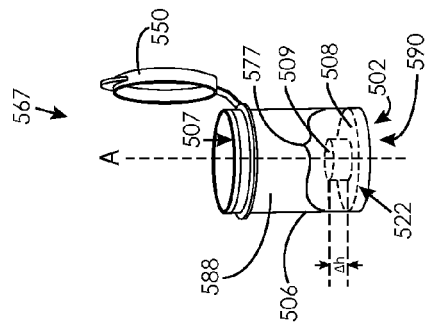
FIGS. 11B and 11C illustrates a perspective and partial cross-sectional view of an analyte test strip container system shown in FIG. 10A after the insert is situated within the cavity and analyte test strips disposed thereon, according to certain embodiments.
Figure 11C:
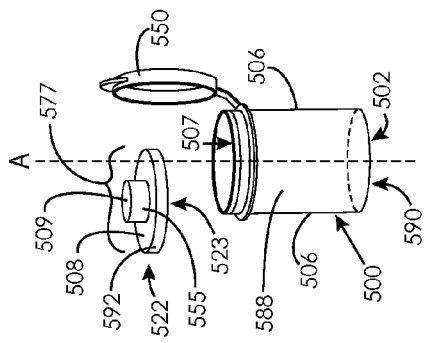

FIG. 11A illustrates a perspective view of an analyte test strip container before an insert is situated within the cavity of the container, according to certain embodiments. FIGS. 11B and 11C illustrates a perspective and partial cross-sectional view, respectively, of an analyte test strip container system shown in FIG. 11A after the insert is situated within the cavity and analyte test strips disposed thereon, according to certain embodiments. FIGS. 11A, 11B, and 11C are described together in the following paragraphs.

As shown, analyte test strip container system 567 comprises insert 522 that is inserted and situated within container 500. Container 500 is shown comprising a base 502 at a proximal end 590, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising a proximal side 523 and an interior side 577. The proximal side 523 faces and abuts the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the interior side 577 of the insert 522 forms all of the cavity floor. The interior side 577 of the insert 522 varies in height with respect to longitudinal axis A, which extends through the opening 507 and the base 502 of the container 500.

The interior side 577 of the insert 522 includes two supporting surfaces 508 and 509 that each support a respective plurality of analyte test strips when disposed in the container 500. Supporting surface 509 is at a higher longitudinal height in the container 500 than supporting surface 508—longitudinally offset by a distance Δh.

In the embodiment shown, the insert 522 is shown comprising a disc shaped securing member 592 and protrusion 555 extending distally from the securing member 592. Protrusion 555 includes circular shaped supporting surface 509, and securing member 592 comprises ring shaped supporting surface 508.

Supporting surface 509 is planar and level. Supporting surface 509 comprises a raised circular surface located concentrically in the circular contour of the supporting surface 508 of the container 500. Supporting surface 508 is also planar and level. Supporting surface 508 is comprised of the unraised surface of the base 502, shaped as a ring located concentrically around the outside of the first supporting surface 509.

The analyte test strips 501B that are disposed on the supporting surface 509 are disposed higher within the cavity 577 of the container 500 than the analyte test strips 501A that are disposed on the supporting surface 508. The difference in height Δh between analyte test strips 501A and 501B corresponds with the longitudinal offset height Δh between the supporting surface 508 and supporting surface 509. The difference in height Δh between the analyte test strips 501A and 501B creates an offset region 511 next to the distal ends of some of the analyte test strips 501B that are disposed adjacent to and higher than the analyte test strips 501A. This enables the user to insert a finger into the offset region 511 region to grip a side 510 of the distal end of a selected analyte test strip 566 that is adjacent to the offset region 511 on supporting surface 509. The user may then pull the selected analyte test strip 566 away from analyte test strips 501B and out the opening 507 of the container 500. The offset region 511 should be wide enough to permit a user's finger to be inserted alongside the analyte test strips that are adjacent to offset region 511. Furthermore, the height of the offset region 511 and longitudinal offset height Δh may vary in size but should be large enough to expose a sufficient amount of the side 510 of the distal end of the analyte test strips that are adjacent to offset region 511 to permit the user's finger to sufficiently grip the side 510 a selected analyte test strip 566.

The offset region 511 enables the user to apply force against the side 510 of the selected analyte test strip 566 as well as towards the opening 507 of the container 500 to displace the analyte test strip 566 away from the analyte test strips 501B. In this way, the user may sufficiently displace the analyte test strip 566 from the analyte test strips 501B to grab it—e.g., by pinching the analyte test strip 566 between the thumb and finger used to displace the test strip 566.

Additional embodiments are shown below. It should be appreciated that the following embodiments are exemplary and the underlying principles of the present disclosure are not limited to the illustrated embodiments. Furthermore, it should be appreciated that some supporting surfaces described in the exemplary figures for analyte test strip container systems may function similar to the supporting surfaces described above in FIGS. 4-9. For the sake of brevity, some repetitive features are not identified or described again.

Figure 12A:
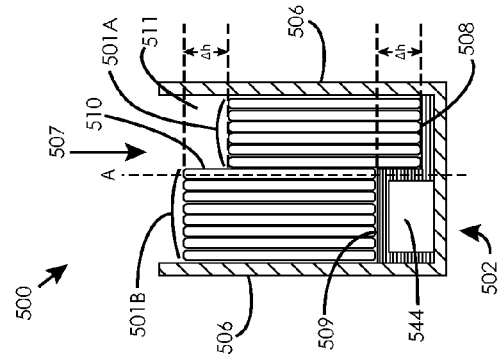
FIG. 12A illustrates a perspective view of an analyte test strip container and insert before the insert is situated within the cavity of the container, according to certain embodiments.
Figure 12B:
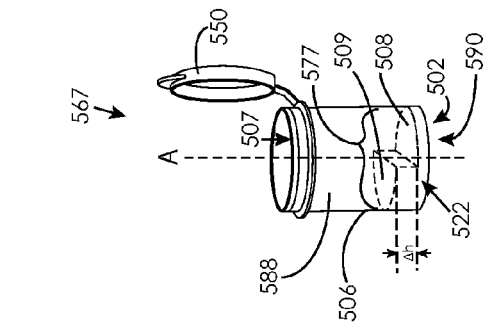
FIGS. 12B and 12C illustrates a perspective and partial cross-sectional view of an analyte test strip container system shown in FIG. 11A after the insert is situated within the cavity and analyte test strips disposed thereon, according to certain embodiments.
Figure 12C:
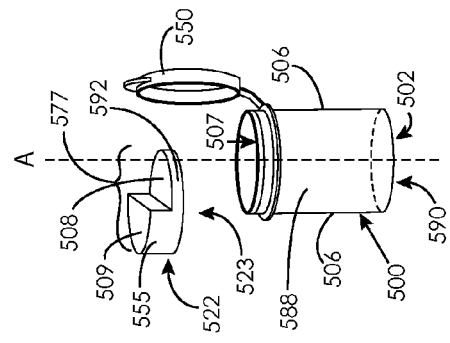

FIG. 12A illustrates a perspective view of an analyte test strip container before an insert is situated within the cavity of the container, according to certain embodiments. FIGS. 12B and 12C illustrates a perspective and partial cross-sectional view of an analyte test strip container system shown in FIG. 12A after the insert is situated within the cavity and analyte test strips disposed thereon, according to certain embodiments. FIGS. 12A, 12B, and 12C are described together in the following paragraphs.

As shown, analyte test strip container system 567 comprises insert 522 that is inserted and situated within container 500. Container 500 is shown comprising a base 502 at a proximal end, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising a proximal side 523 and an interior side 577. The proximal side 523 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the interior side 577 of the insert 522 forms all of the cavity floor. The interior side 577 of the insert 522 varies in height with respect to longitudinal axis A, which extends through the opening 507 and the base 502 of the container 500.

The interior side 577 of insert 522 includes a first supporting surface 508 and a second supporting surface 509 that each support a respective plurality of analyte test strips when disposed in the container 500. Supporting surface 509 is at a higher longitudinal height in the container 400 than supporting surface 508; and further, is longitudinally offset by a distance Δh.

In the embodiment shown, the insert 522 is shown comprising a disc shaped securing member 592 and protrusion 555 extending distally from the securing member 592. Protrusion 555 includes semi-circular shaped supporting surface 509, and securing member 592 comprises semi-circular shaped supporting surface 508. Insert 522 is also shown in this embodiment to include a recess or indentation 544, as shown in FIG. 544, that corresponds to the formation of the raised supporting surface 509. It should be appreciated that in other embodiments, the insert 522 may not include recess or indentation 544, as shown in other figures for example.

Supporting surface 508 and supporting surface 509 are longitudinally offset from one another, and are each planar and level. Supporting surface 509 is a raised semi-circular shaped surface that is longitudinally offset a distance of Δh from supporting surface 508, which also has a semi-circular shape. The analyte test strip 501A on supporting surface 508 are disposed in the container 500 at a lower height than the analyte test strips 501B on the supporting surface 509. The offset region 511 formed by the longitudinal offset exposes a side 510 of some of the higher analyte test strips 501B that are adjacent to the offset region 511. Accordingly, the user may grip the side 510 of an exposed test strip and pull it away from the analyte test strips 501B.

FIG. 13A illustrates a perspective view of an analyte test strip container before an insert is situated within the cavity of the container, according to certain embodiments. FIGS. 13B and 13C illustrates a perspective and partial cross-sectional view of an analyte test strip container system shown in FIG. 13A after the insert is situated within the cavity and analyte test strips disposed thereon, according to certain embodiments. FIGS. 13A, 13B, and 13C are described together in the following paragraphs.

As shown, analyte test strip container system 567 comprises insert 522 that is inserted and situated within container 500. Container 500 is shown comprising a base 502 at a proximal end, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising a proximal side 523 and an interior side 577. The proximal side 523 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the cavity floor 587 comprises the interior side 577 of the insert 522 and the uncovered part of the interior side of the base 502. The cavity floor 587 varies in height with respect to longitudinal axis A, which extends through the opening 507 and the base 502 of the container 500.

The interior side 577 of insert 522 serves as supporting surface 508 that supports a plurality of analyte test strips 501A when disposed in the container 500. The uncovered part of the interior side of base 502 serves as supporting surface 508 that supports a plurality of analyte test strips 501B when disposed in the container 500. Supporting surface 509 is at a higher longitudinal height in the container 500 than supporting surface 508; and further, is longitudinally offset by a distance Δh.

In the embodiment shown, the shape of the insert 522 may enable the body 542 of the insert 522 to serve as the securing member. As stated before, the contour of the insert 522 may be shaped and sized to fit within the contours of the cavity such that the insert is generally fixed when situated within the container 500. For example, the insert may be sized to be half the size of the base—e.g., a semi-circular or semi-elliptical insert that is slightly smaller than a circular or elliptical base—or even greater than half the size and shape of the base.

Supporting surface 508 and supporting surface 509 are longitudinally offset from one another. Supporting surface 508 is planar and level, and supporting surface 509 is planar and angled. Supporting surface 509 is a semi-circular shaped surface that is longitudinally offset a distance of Δh from supporting surface 508, which also has a semi-circular shape. The analyte test strip 501A on supporting surface 508 are disposed in the container 500 at a lower height than the analyte test strips 501B on the supporting surface 509. The offset region 511 formed by the longitudinal offset exposes a side 510 of some of the higher analyte test strips 501B that are adjacent to the offset region 511. Accordingly, the user may grip the side 510 of an exposed test strip and pull it away from the analyte test strips 501B.

FIG. 14A illustrates a perspective view of an analyte test strip container before an insert is situated within the cavity of the container, according to certain embodiments. FIGS. 14B and 14C illustrates a perspective and partial cross-sectional view of an analyte test strip container system shown in FIG. 14A after the insert is situated within the cavity and analyte test strips disposed thereon, according to certain embodiments. FIGS. 14A, 14B, and 14C are described together in the following paragraphs.

As shown, analyte test strip container system 567 comprises insert 522 that is inserted and situated within container 500. Container 500 is shown comprising a base 502 at a proximal end, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising a proximal side 523 and an interior side 577. The proximal side 523 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the interior side 577 of the insert 522 forms all of the cavity floor. The interior side 577 of the insert 522 varies in height with respect to longitudinal axis A, which extends through the opening 507 and the base 502 of the container 500.

The interior side 577 of insert 522 forms the cavity floor and is comprised of a supporting surface 508A, a supporting surface 508B, and supporting surface 509 that each support a respective plurality of analyte test strips when disposed in the container 500. Supporting surface 509 is at a different longitudinal height in the container 500 than supporting surfaces 508A and 508B—longitudinally offset by a distance Δh.

In the embodiment shown, the insert 522 is shown comprising a disc shaped securing member 592 and protrusion 555 extending distally from the securing member 592. Protrusion 555 includes ring shaped supporting surface 509, and securing member 592 comprises ring shaped supporting surface 508A and circular shaped supporting surface 508B.

Supporting surface 508A, a supporting surface 508B, and supporting surface 509 are each planar and level. Supporting surface 509 is a raised ring shaped surface that is longitudinally offset a distance of Δh from supporting surfaces 508A and 508B. Supporting surface 508A is a surface of the insert 522 located concentrically around the outside of the ring shaped supporting surface 509. Further, supporting surface 508B is a surface of the insert 522 located concentrically within the ring shaped supporting surface 509.

The analyte test strips 501A on supporting surfaces 508A and 508B are disposed in the container 500 at a lower height than the analyte test strips 501B on the supporting surface 509. The offset regions 511 are formed by the longitudinal offsets and expose a side 510 of some of the higher analyte test strips 501B that are adjacent to the offset regions 511. Accordingly, the user may grip the side 510 of an exposed test strip and pull it away from the analyte test strips 5401B. It should be appreciated that in certain embodiments one offset region may be different shaped or sized from another offset region.

Figure 15A:
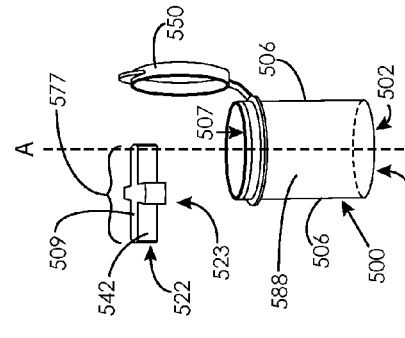
FIG. 15A illustrates a perspective view of an analyte test strip container and insert before the insert is situated within the cavity of the container, according to certain embodiments.
Figure 15B:
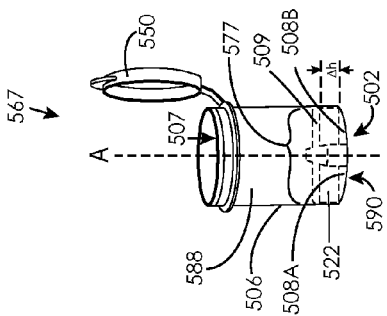
FIGS. 15B and 15C illustrates a perspective and partial cross-sectional view of an analyte test strip container system shown in FIG. 14A after the insert is situated within the cavity and analyte test strips disposed thereon, according to certain embodiments.
Figure 15C:
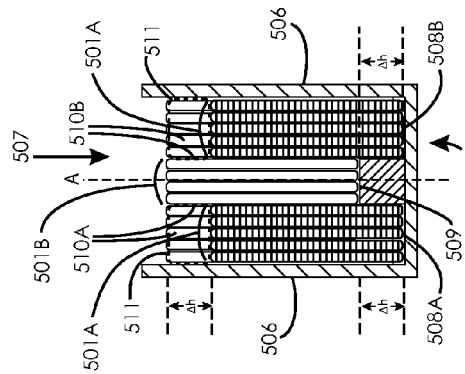

FIG. 15A illustrates a perspective view of an analyte test strip container before an insert is situated within the cavity of the container, according to certain embodiments. FIGS. 15B and 15C illustrates a perspective and partial cross-sectional view of an analyte test strip container system shown in FIG. 15A after the insert is situated within the cavity and analyte test strips disposed thereon, according to certain embodiments. FIGS. 15A, 15B, and 15C are described together in the following paragraphs.

As shown, analyte test strip container system 567 comprises insert 522 that is inserted and situated within container 500. Container 500 is shown comprising a base 502 at a proximal end, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising a proximal side 523 and an interior side 577. The proximal side 523 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the interior side 577 of the insert 522 forms all of the cavity floor. The interior side 577 of the insert 522 varies in height with respect to longitudinal axis A, which extends through the opening 507 and the base 502 of the container 500.

The interior side 577 of insert 522 forms the cavity floor and is comprised of a supporting surface 508A, supporting surface 508B, supporting surface 508C (not shown), supporting surface 408D (not shown), and supporting surface 509 that each support a respective plurality of analyte test strips when disposed in the container 500. Supporting surface 509 is at a different longitudinal height in the container 400 than supporting surfaces 508A, 508B, 508C, and 508D—longitudinally offset by a distance Δh.

In the embodiment shown, the insert 522 is shown comprising a disc shaped securing member 592 and protrusion 555 extending distally from the securing member 592. Protrusion 555 includes cross-shaped supporting surface 509, and securing member 592 comprises the four supporting surfaces 508A, 508B, 508C, and 508D.

Supporting surfaces 508A, 508B, 508C, and 508D, as well as supporting surface 509, are each planar and level. Supporting surface 509 is a raised cross shaped surface that is longitudinally offset a distance of Δh from supporting surfaces 508A, 508B, 508C, and 508D. The raised surface is shown as two rectangular raised strips crossing one another and delineating four quadrants of the supporting surfaces 508A, 508B, 508C, and 508D. The analyte test strips 501A on the supporting surfaces 508A, 508B, 508C, and 508D are disposed in the container 500 at a different height than the analyte test strips 501B on the supporting surface 509. It is noted that in FIG. 14C, analyte test strips 501A are illustrated with vertically hatched lines and are shown for only two supporting surface 508A and 508B since the other two supporting surfaces 508C and 508D are not shown.

The analyte test strips 501A on supporting surfaces 508A, 508B, 508C, and 508D are disposed in the container 500 at a lower height than the analyte test strips 501B on the supporting surface 509. The offset regions 511 are formed by the longitudinal offsets and expose a side 510 of some of the higher analyte test strips 501B that are adjacent to the offset regions 511. Accordingly, the user may grip the side 510 of an exposed test strip and pull it away from the analyte test strips 501B. It should be appreciated that in certain embodiments one offset region may be different shaped or sized from another offset region.

Figure 16A:
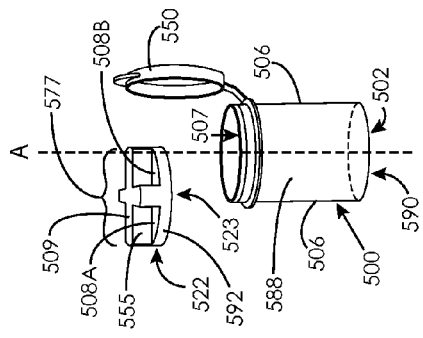
FIG. 16A illustrates a perspective view of an analyte test strip container and insert before the insert is situated within the cavity of the container, according to certain embodiments.
Figure 16B:
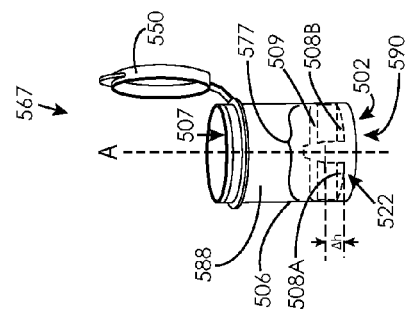
FIGS. 16B and 16C illustrates a perspective and partial cross-sectional view of an analyte test strip container system shown in FIG. 15A after the insert is situated within the cavity and analyte test strips disposed thereon, according to certain embodiments.
Figure 16C:
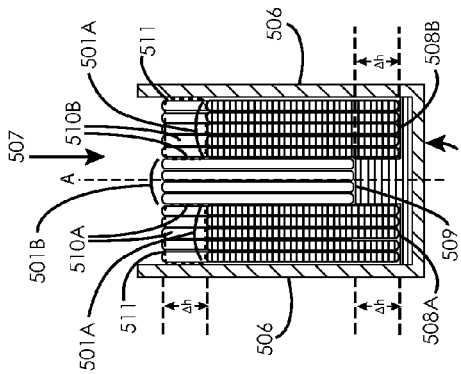

FIG. 16A illustrates a perspective view of an analyte test strip container before an insert is situated within the cavity of the container, according to certain embodiments. FIGS. 16B and 16C illustrates a perspective and partial cross-sectional view of an analyte test strip container system shown in FIG. 16A after the insert is situated within the cavity and analyte test strips disposed thereon, according to certain embodiments. FIGS. 16A, 16B, and 16C are described together in the following paragraphs.

As shown, analyte test strip container system 567 comprises insert 522 that is inserted and situated within container 500. Container 500 is shown comprising a base 502 at a proximal end, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising a proximal side 523 and an interior side 577. The proximal side 523 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the cavity floor 587 comprises the interior side 577 of the insert 522 and the uncovered part of the interior side of the base 502. The cavity floor 587 varies in height with respect to longitudinal axis A, which extends through the opening 507 and the base 502 of the container 500.

The interior side 577 of insert 522 serves as supporting surface 508 that supports a plurality of analyte test strips 501A when disposed in the container 500. The uncovered part of the interior side of base 502 serves as supporting surface 508 that supports a plurality of analyte test strips 501B when disposed in the container 500. Supporting surface 509 is at a higher longitudinal height in the container 500 than supporting surface 508; and further, is longitudinally offset by a distance Δh.

The uncovered portion of the interior side of base 502 is comprised of a supporting surface 508A, supporting surface 508B, supporting surface 508C (not shown), and supporting surface 508D (not shown) that each support a respective plurality of analyte test strips when disposed in the container 500. The interior side 577 of base 502 includes supporting surface 509 that supports a respective plurality of analyte test strips when disposed in the container 500. Supporting surface 509 is at a different longitudinal height in the container 400 than supporting surfaces 508A, 508B, 508C, and 508D—longitudinally offset by a distance Δh.

In the embodiment shown, the shape of the insert 522 may enable the body 542 of the insert 522 to serve as the securing member. As stated before, the contour of the insert 522 may be shaped to fit within the contours of the cavity such that the insert is generally fixed when situated within the container 500. For example, the insert may be cross shaped and sized to span to the perimeter of a circular base. In such cases, the insert may still be shaped and sized to remain relatively fixed within the container.

Supporting surfaces 508A, 508B, 508C, and 508D, as well as supporting surface 509, are each planar and level. Supporting surface 509 is a raised cross shaped surface that is longitudinally offset a distance of Δh from supporting surfaces 508A, 508B, 508C, and 508D. The raised surface is shown as two rectangular raised strips crossing one another and delineating four quadrants of the supporting surfaces 508A, 508B, 508C, and 508D. The analyte test strips 501A on the supporting surfaces 508A, 508B, 508C, and 508D are disposed in the container 500 at a different height than the analyte test strips 501B on the supporting surface 509. It is noted that in FIG. 15C, analyte test strips 501A are illustrated with vertically hatched lines and are shown for only two supporting surface 508A and 508B since the other two supporting surfaces 508C and 508D are not shown.

The analyte test strips 501A on supporting surfaces 508A, 508B, 508C, and 508D are disposed in the container 500 at a lower height than the analyte test strips 501B on the supporting surface 509. The offset regions 511 are formed by the longitudinal offsets and expose a side 510 of some of the higher analyte test strips 501B that are adjacent to the offset regions 511. Accordingly, the user may grip the side 510 of an exposed test strip and pull it away from the analyte test strips 501B. It should be appreciated that in certain embodiments one offset region may be different shaped or sized from another offset region.

FIG. 17A illustrates a perspective view of an analyte test strip container before an insert is situated within the cavity of the container, according to certain embodiments. FIGS. 17B and 17C illustrates a perspective and partial cross-sectional view of an analyte test strip container system shown in FIG. 17A after the insert is situated within the cavity and analyte test strips disposed thereon, according to certain embodiments. FIGS. 17A, 17B, and 17C are described together in the following paragraphs.

As shown, analyte test strip container system 567 comprises insert 522 that is inserted and situated within container 500. Container 500 is shown comprising a base 502 at a proximal end, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising a proximal side 523 and an interior side 577. The proximal side 523 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the interior side 577 of the insert 522 forms all of the cavity floor. The interior side 577 of the insert 522 varies in height with respect to longitudinal axis A, which extends through the opening 507 and the base 502 of the container 500.

The interior side 577 of base 502 forms the cavity floor and is comprised of a supporting surface 508A, supporting surface 509A, and supporting surface 509B that each support a respective plurality of analyte test strips when disposed in the container 500. Supporting surface 509A is at a higher longitudinal height in the container 400 than supporting surface 508—longitudinally offset by a distance $\Delta h1$. Further, supporting surface 509B is at a higher longitudinal height in the container 500 than supporting surface 509A—longitudinally offset by a distance $\Delta h2$.

In the embodiment shown, the insert 522 is shown comprising a disc shaped securing member 592 and protrusion 555 extending distally from the securing member 592. Protrusion 555 includes supporting surfaces 509A and 509B, and securing member 592 comprises semi-circular shaped supporting surface 508.

Supporting surfaces 508, 509A, and 509B are each planar and level. Supporting surfaces 509A and 509B form raised step-like surfaces that increment in height to provide longitudinal offsets $\Delta h1$ and $\Delta h2$. The analyte test strips 501A on supporting surface 508 are disposed in the container 500 at a lower height than the analyte test strips 501B on the supporting surface 509A. The offset region 511A is formed by the longitudinal offset $\Delta h1$ and exposes a side 510A of some of the higher analyte test strips 501B that are adjacent to the offset region 511A. Accordingly, the user may grip the side 510A of an exposed test strip and pull it away from the analyte test strips 501B.

Furthermore, the analyte test strips 501B on supporting surface 509A are disposed in the container 500 at a lower height than the analyte test strips 501C on the supporting surface 509B. The offset region 511B is formed by the longitudinal offset $\Delta h2$ and exposes a side 510B of some of the higher analyte test strips 501C that are adjacent to the offset region 511B. Accordingly, the user may grip the side 510B of an exposed test strip and pull it away from the analyte test strips 501C.

FIG. 18A illustrates a perspective view of an analyte test strip container before an insert is situated within the cavity of the container, according to certain embodiments. FIGS. 18B and 18C illustrates a perspective and partial cross-sectional view of an analyte test strip container system shown in FIG. 18A after the insert is situated within the cavity and analyte test strips disposed thereon, according to certain embodiments. FIGS. 18A, 18B, and 18C are described together in the following paragraphs.

As shown, analyte test strip container system 567 comprises insert 522 that is inserted and situated within container 500. Container 500 is shown comprising a base 502 at a proximal end, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising a proximal side 523 and an interior side 577. The proximal side 523 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the cavity floor 587 comprises the interior side 577 of the insert 522 and the uncovered part of the interior side of the base 502. The cavity floor 587 varies in height with respect to longitudinal axis A, which extends through the opening 507 and the base 502 of the container 500.

The interior side 577 of base 502 is comprised of supporting surface 509A and supporting surface 509B that each support a respective plurality of analyte test strips when disposed in the container 500. The uncovered part of the interior side of the base 502 is comprised of supporting surface 508. Supporting surface 509A is at a higher longitudinal height in the container 400 than supporting surface 508—longitudinally offset by a distance $\Delta h1$. Further, supporting surface 509B is at a higher longitudinal height in the container 500 than supporting surface 509A—longitudinally offset by a distance $\Delta h2$.

In the embodiment shown, the shape of the insert 522 may enable the body 542 of the insert 522 to serve as the securing member. As stated before, the contour of the insert 522 may be shaped to fit within the contours of the cavity such that the insert is generally fixed when situated within the container 500.

Supporting surfaces 508, 509A, and 509B are each planar and level. Supporting surfaces 509A and 509B form raised step-like surfaces that increment in height to provide longitudinal offsets $\Delta h1$ and $\Delta h2$. The analyte test strips 501A on supporting surface 508 are disposed in the container 500 at a lower height than the analyte test strips 501B on the supporting surface 509A. The offset region 511A is formed by the longitudinal offset $\Delta h1$ and exposes a side 510A of some of the higher analyte test strips 501B that are adjacent to the offset region 511A. Accordingly, the user may grip the side 510A of an exposed test strip and pull it away from the analyte test strips 501B.

Furthermore, the analyte test strips 501B on supporting surface 509A are disposed in the container 500 at a lower height than the analyte test strips 501C on the supporting surface 509B. The offset region 511B is formed by the longitudinal offset Δh2 and exposes a side 510B of some of the higher analyte test strips 501 C that are adjacent to the offset region 511B. Accordingly, the user may grip the side 510B of an exposed test strip and pull it away from the analyte test strips 501C.

As stated before, it should be appreciated that various combinations of shapes, types, and orientations of supporting surfaces may be implemented—e.g., on the interior side of the base of a container, and/or on the interior side of an insert (described in further detail later). The following figures are provided to illustrate additional variations, but for the sake of brevity, a detailed analysis is not provided. It should be appreciated that the supporting surfaces and longitudinal offsets function in similar ways as those described above to enable a user to be able to displace and grab analyte test strips from the container.

Figure 19:
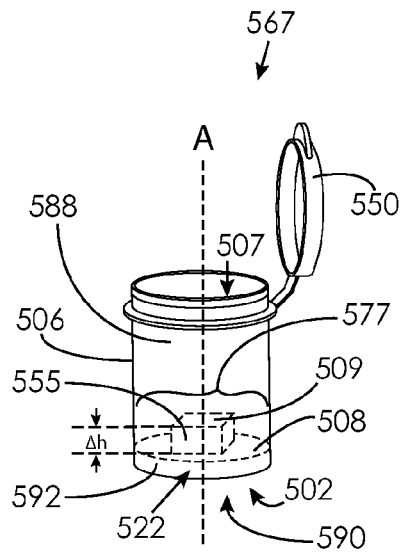
FIG. 19 illustrates a perspective view of an analyte test strip container system, according to certain embodiments.

FIG. 19 illustrates a perspective view of an analyte test strip container system, according to certain embodiments. As shown, analyte test strip container system 567 comprises insert 522 that is inserted and situated within container 500.

Container 500 is shown comprising a base 502 at a proximal end, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

When the insert 522 is situated within the cavity 588, the interior side 577 of the insert 522 forms all of the cavity floor. The interior side 577 of the insert 522 varies in height with respect to longitudinal axis A, which extends through the opening 507 and the base 502 of the container 500.

The interior side 577 of the insert 522 includes two supporting surfaces 508 and 509 that each support a respective plurality of analyte test strips when disposed in the container 500. Supporting surface 509 is at a higher longitudinal height in the container 500 than supporting surface 508—longitudinally offset by a distance Δh.

In the embodiment shown, the insert 522 is shown comprising a disc shaped securing member 592 and protrusion 555 extending distally from the securing member 592. Protrusion 555 includes square shaped supporting surface 509, and securing member 592 comprises supporting surface 508 that is circularly shaped around protrusion 555.

Supporting surface 509 is planar and level. Supporting surface 509 comprises a raised square surface located in the center of the circular contour of the supporting surface 508. Supporting surface 508 is also planar and level. Supporting surface 508 is an unraised surface of the insert 522 located around the outside of the first supporting surface 509.

The analyte test strips 501B that are disposed on the supporting surface 509 are disposed higher within the cavity 577 of the container 500 than the analyte test strips 501A that are disposed on the supporting surface 508. The difference in height Δh between analyte test strips 501A and 501B corresponds with the longitudinal offset height Δh between the supporting surface 508 and supporting surface 509.

Figure 20:
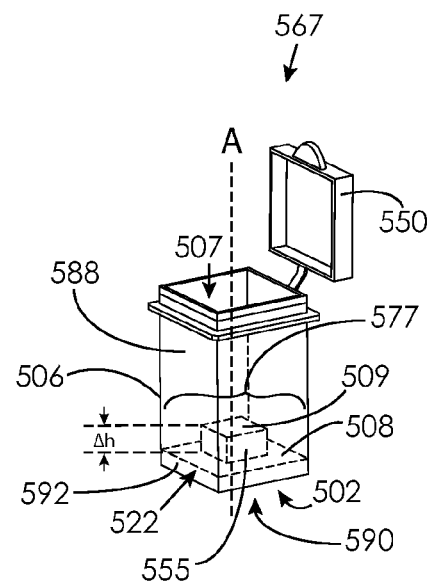
FIG. 20 illustrates a perspective view of an analyte test strip container system, according to certain embodiments.

FIG. 20 illustrates a perspective view of an analyte test strip container system, according to certain embodiments. As shown, analyte test strip container system 567 comprises insert 522 that is inserted and situated within container 500.

Container 500 is shown comprising a square base 502 at a proximal end, four sidewalls 506A, 506B, 506C, and 506D extending from the square base 502 forming a cavity 588 and opening 507 at a distal end 599. Container 500 is also shown comprising a cap 550 that closes the container 500 and may provide a sealed environment for the analyte test strips disposed therein. When the insert 522 is situated within the cavity 588, the interior side 577 of the insert 522 forms all of the cavity floor. The interior side 577 of the insert 522 varies in height with respect to longitudinal axis A, which extends through the opening 507 and the base 502 of the container 500.

The interior side 577 of the insert 522 includes two supporting surfaces 508 and 509 that each support a respective plurality of analyte test strips when disposed in the container 500. Supporting surface 509 is at a higher longitudinal height in the container 500 than supporting surface 508—longitudinally offset by a distance Δh.

In the embodiment shown, the insert 522 is shown comprising a square shaped securing member 592 and protrusion 555 extending distally from the securing member 592. Protrusion 555 includes square shaped supporting surface 509, and securing member 592 comprises supporting surface 508 that is square shaped around protrusion 555.

Supporting surface 509 is planar and level. Supporting surface 509 comprises a raised square surface located concentrically in the square contour of the supporting surface 508. Supporting surface 508 is also planar and level. Supporting surface 508 is an unraised surface of the insert 522 located around the outside of the first supporting surface 509.

The analyte test strips 501B that are disposed on the supporting surface 509 are disposed higher within the cavity 577 of the container 500 than the analyte test strips 501A that are disposed on the supporting surface 508. The difference in height Δh between analyte test strips 501A and 501B corresponds with the longitudinal offset height Δh between the supporting surface 508 and supporting surface 509.

In certain embodiments, the cavity floor may include a single supporting surface that is angled sufficiently to displace analyte test strips in height from one another to create sufficient difference in heights between test strips to enable a user to grip a test strip and to displace it away from the other analyte test strips. Example angles may range from, for example, 10 degrees to 80 degrees, such as 15 degrees to 75 degrees, including 30 degrees to 60 degrees. This applies to containers described above that do not have an insert but rather have an interior side of the base that forms the cavity floor. It also applies to the inserts, and container systems including an insert, that have interior sides of the insert that form all of the cavity floor, as described above.

Figure 21A:
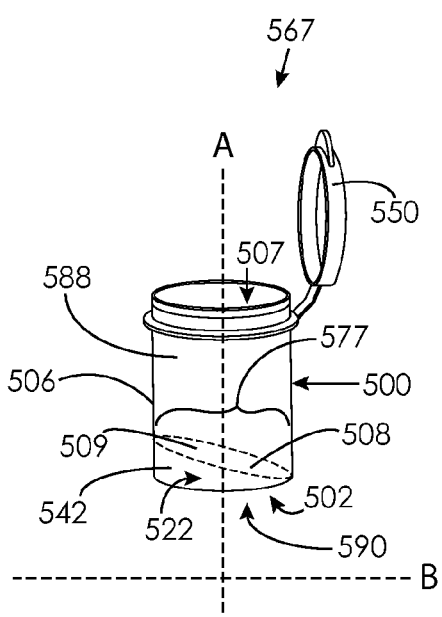
FIGS. 21A-21B illustrate a perspective view and partial cross sectional view of an analyte test strip container system, according to certain embodiments.
Figure 21B:
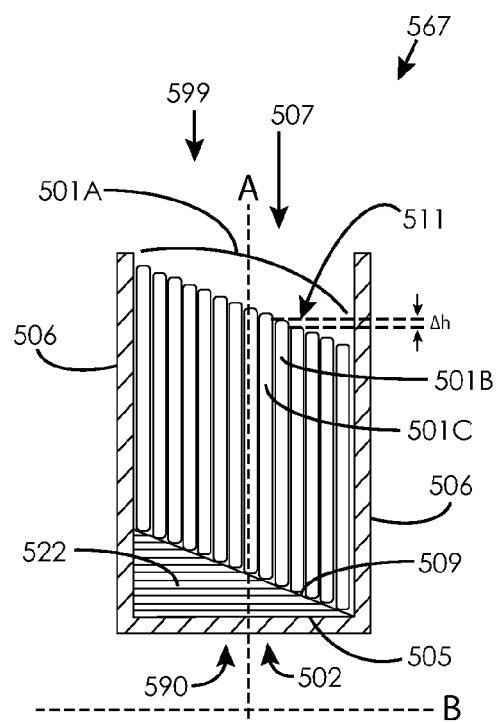

For example, FIGS. 21A-21B illustrate a perspective view and partial cross sectional view of an analyte test strip container system, according to certain embodiments. As shown, analyte test strip container system 567 comprises insert 522 that is inserted and situated within container 500. Container 500 is shown comprising a base 502 at a proximal end 590, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising an interior side 577. A proximal side of the insert 522 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, the interior side 577 of the insert 522 forms all of the cavity floor 587, as shown. The interior side 577 of the insert varies in height with respect to longitudinal axis A, which extends through the opening 507 and the base 502 of the container 500.

The interior side 577 of insert 522 serves as supporting surface 509 that supports a plurality of analyte test strips 501A when disposed in the container 500. Supporting surface 509 is angled sufficiently in the container 500 to make adjacent analyte test strips to be at different heights longitudinally offset by a distance Δh. It should be understood that the term "angled" is used herein with respect to a latitudinal axis B that is level and perpendicular to the longitudinal axis A.

In the embodiment shown, the shape of the insert 522 may enable the body 542 of the insert 522 to serve as the securing member. As stated before, the contour of the insert 522 may be shaped to fit within the contours of the cavity such that the insert is generally fixed when situated within the container 500.

Supporting surface 509 is an elliptically shaped surface (circularly shaped if viewed from a top view) that angled from latitudinal axis A. The analyte test strip 501B on supporting surface 509 is disposed in the container 500 adjacent to and lower in height than analyte test strip 501C on supporting surface 509. The difference in height Δh between the test strips 501B and 501C exposes a side 510 of higher analyte test strip 501C. Accordingly, the user may grip the side 510 of an exposed test strip and pull it away from the analyte test strips 501A.

In certain embodiments, the interior side of the base may comprise two or more supporting surfaces that are not longitudinally offset (e.g., a space or gap in longitudinal height does not exist between the two adjacent supporting surfaces). For example, the two supporting surfaces may be individually distinct from one another but meet or join one another at the same longitudinal height—e.g., two angled surfaces that are not in the same plane but meet at the same height, such as to form a v-shape or upside down v-shape.

Figure 22A:
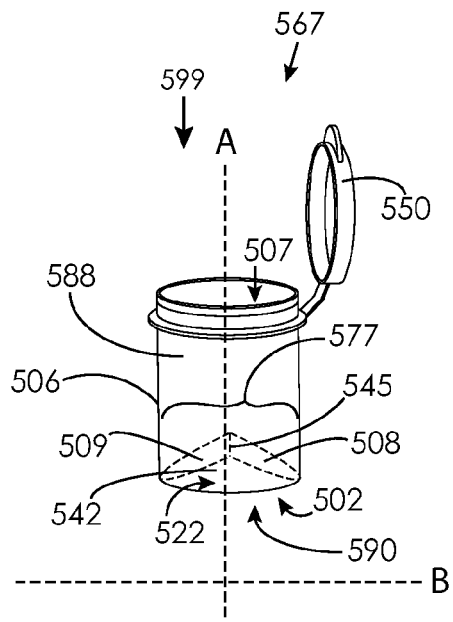
FIGS. 22A-22B illustrate a perspective view and partial cross sectional view of an analyte test strip container system, according to certain embodiments.
Figure 22B:
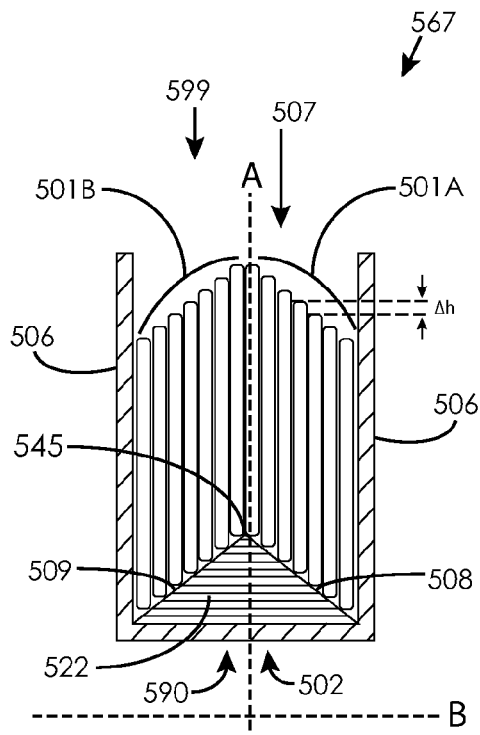

For example, FIGS. 22A-22B illustrate a perspective view and partial cross sectional view of an analyte test strip container system, according to certain embodiments. As shown, analyte test strip container system 567 comprises insert 522 that is inserted and situated within container 500. Container 500 is shown comprising a base 502 at a proximal end 590, sidewall 506 extending from the base 502 forming a cavity 588 and opening 507 at a distal end 599. Container 500 is also shown comprising a cap 550 that closes the container 500 and may provide a sealed environment for the analyte test strips disposed therein.

Insert 522 is shown comprising an interior side 577. A proximal side of insert 522 faces the base 502 of the container 500 when inserted and situated within the cavity 588 of the container 500. The interior side 577 of the insert 522 faces the opening 507 of the cavity 488 when situated within the cavity 588.

When the insert 522 is situated within the cavity 588, as shown, the interior side 577 of the insert 522 forms all of the cavity floor. The interior side 577 of the insert 522 varies in height with respect to longitudinal axis A, which extends through the opening 507 and the base 502 of the container 500.

In the embodiment shown, the shape of the insert 522 may enable the body 542 of the insert 522 to serve as the securing member. As stated before, the contour of the insert 522 may be shaped to fit within the contours of the cavity such that the insert is generally fixed when situated within the container 500.

The interior side 577 of insert 522 includes a first supporting surface 508 and a second supporting surface 509 that each support a respective plurality of analyte test strips 501A and 501B, respectively, when disposed in the container 500. Supporting surface 508 is planar and angled with respect to the latitudinal axis B. Supporting surface 509 is also planar and angled with respect to the latitudinal axis B. Supporting surface 509 is at the same longitudinal height in the container 500 than supporting surface 508.

Supporting surfaces 508 and 509 are raised partially elliptical shaped surfaces that are oppositely angled with respect to each other. The two surfaces 508 and 509 meet at a common point 545 and have the same height, and thus are not longitudinally offset from one another.

Supporting surface 509 is angled sufficiently in the container 500 to make adjacent analyte test strips disposed on supporting surface 509 to be at different heights longitudinally offset by a distance Δh. Similarly, supporting surface 508 is angled sufficiently in the container 500 to make adjacent analyte test strips disposed on supporting surface 508 to be at different heights longitudinally offset by a distance Δh. It should be appreciated that in other embodiments, one supporting surface may be angled to a different degree than the other supporting surface. It should also be appreciated that in other embodiments, additional supporting surfaces may be implemented.

In certain embodiments, a supporting surface may provide for a latitudinal offset between analyte test strips on one or more supporting surfaces. The term "latitudinally offset" is used herein to refer to latitudinal space or gap in latitudinal width between adjacent analyte test strips on one or more supporting surfaces. The latitudinal width is measured with respect to a latitudinal axis that is perpendicular to the longitudinal axis. The latitudinal offset enables the analyte test strips disposed next to the spacer to be sufficiently spaced apart latitudinally from other analyte test strips disposed next to the spacer, exposing enough of the sides of analyte test strips next to the space to permit a user to grip one of the analyte test strips.

For example, a spacer may be positioned between the first and second supporting surfaces to provide space between the two pluralities of analyte test strips disposed respectively thereon. As another example, the spacer may be positioned on one supporting surface to provide space between analyte tests disposed on the supporting surface next to the spacer. The spacer may be, for instance, a protrusion, bump, projection, etc., that may separate the analyte test strips on one or more supporting surfaces. The spacer may take any variety of shapes and sizes—e.g., cone or frustum shaped, cylindrical shaped, cube shaped, ring shaped, etc. It should be appreciated that in some embodiments, more than one spacer may be present.

In some instances, the spacer includes a distal surface that prevents analyte test strips from being disposed thereon—e.g., a cone shaped spacer with the point facing the opening of the container. In this way, analyte test strips may not inadvertently be disposed on the distal surface of the spacer, but still remain separated by a space latitudinally.

In other instances, the spacer may include a distal surface but have a longitudinal height that prevents the analyte test strips from fitting within the container if disposed on the distal surface of the spacer. In this way, analyte test strips that are inadvertently disposed on the container will be easily identifiable and may be repositioned on supporting surfaces or removed. In some instances, the analyte test strip container may not close if an analyte test strip is disposed on the spacer because the test strip will be extending outside of the opening of the container.

The longitudinal height of the spacer may vary but should be shorter than the distal ends of the analyte test strips so as to create an offset region that is sufficiently large enough to enable a finger tip to sufficiently grip the side of an analyte test strip without be obstructed by the spacer, enabling the user to pull the analyte test strip away from the other analyte test strips and toward the opening of the container. In this way, the user may sufficiently displace the analyte test strip from the other analyte test strips to "grab" it—e.g., by pinching the analyte test strip between the thumb and the finger used to displace it.

Furthermore, the longitudinal height of the spacer should be large enough to prevent an analyte test strip from being disposed on the distal surface of the spacer without extending out of the opening of the cavity of the container, or otherwise preventing the container from being closed. For example, for a container that is approximately 50 mm long and analyte test strips that are approximately 30 mm long, the height of the spacer may range from 2 mm to 28 mm, such as 22 mm to 26 mm, and including 22 mm to 23 mm. It should be appreciated that the thickness of the base of the container, as well as the amount the cap that protrudes into the cavity of the container may affect the ranges of heights of the spacer that are permitted.

The width of the latitudinal offset may vary but should separate the two groups of analyte test strips wide enough to enable a finger tip to be inserted in the space generated between the two groups of analyte test strips. In this way, the user may insert a finger tip into the space to pull the analyte test strip away from the other analyte test strips and toward the opening of the container. Example widths of the latitudinal offsets may range from, for example, 3 mm or more, such as 5 mm or more, including 7 mm or more.

The description herein on spacers may apply to containers described above that do not have an insert but rather have an interior side of the base that forms the cavity floor. For example, the cavity floor may include one or more supporting surfaces that are separated latitudinally by a spacer that extends from the base towards the opening.

The description herein on spacers may also apply to the inserts, and container systems including an insert, as described above. For example, an interior side of an insert may form all of the cavity floor and include one or more supporting surfaces and a spacer. As another example, the interior side of an insert may include a spacer and one or more supporting surfaces that form part of the cavity floor, with the other part of the cavity floor being formed by one or more supporting surface that are on the uncovered portion of the interior of the base. The spacer may, for example, provide latitudinal space between analyte test strips on supporting surfaces on the interior side of the insert, between analyte test strips on supporting surfaces on the interior side base, and/or between analyte test strips on supporting surfaces on the interior side of the insert and on the uncovered portion of the interior side of the base.

Figure 23A:
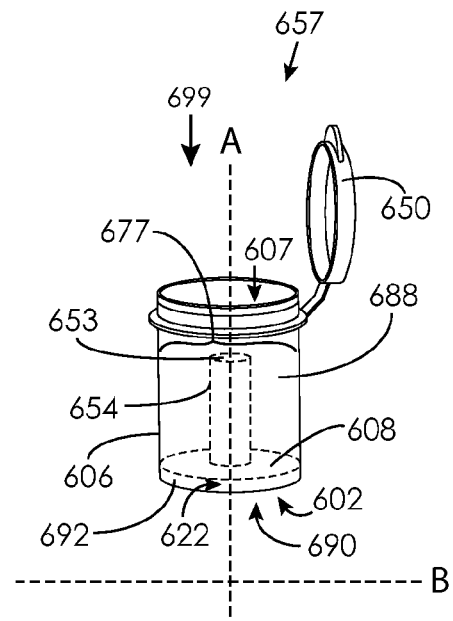
FIGS. 23A-23B a perspective view and partial cross sectional view of an analyte test strip container system, according to certain embodiments.
Figure 23B:
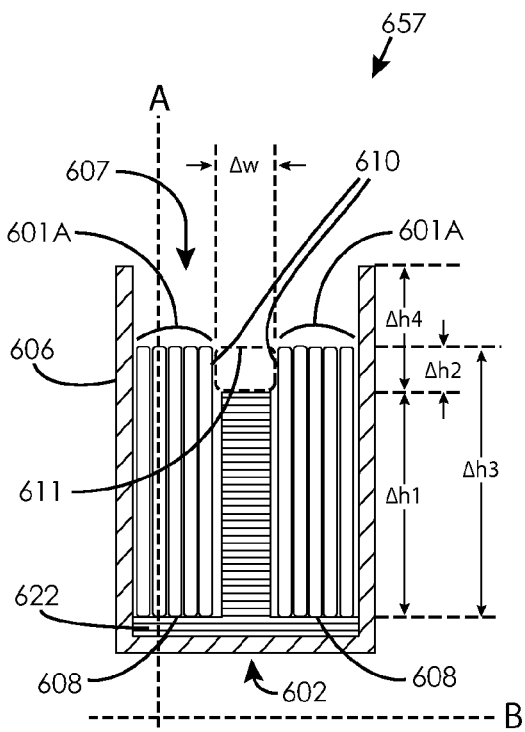

FIGS. 23A-23B a perspective view and partial cross sectional view of an analyte test strip container system, according to certain embodiments.

As shown, analyte test strip container system 657 comprises insert 622 that is inserted and situated within container 600. Container 600 is shown comprising a base 602 at a proximal end 690, sidewall 606 extending from the base 602 forming a cavity 688 and opening 607 at a distal end 699. Container 600 is also shown comprising a cap 650 that closes the container 600 and may provide a sealed environment for the analyte test strips disposed therein.

Insert 622 is shown comprising an interior side 677. The interior side 677 includes supporting surface 608 and spacer 654. A proximal side on insert 622 faces and abuts the base 602 of the container 600 when inserted and situated within the cavity 688 of the container 600. The interior side 677 of the insert 622 faces the opening 607 of the cavity 688 when situated within the cavity 688.

When the insert 622 is situated within the cavity 688, as shown, the interior side 677 of the insert 622 forms all of the cavity floor. The interior side 677 of the insert 622 varies in height with respect to longitudinal axis A, which extends through the opening 607 and the base 602 of the container 500.

Supporting surface 608 supports a plurality of analyte test strips 601A when disposed in the container 600. Spacer 654 is shown having a latitudinal width $\Delta w$ and longitudinal height $\Delta h1$. Spacer 654 is positioned on the interior side 677 of the insert 622 within supporting surface 608 such that the spacer 654 is between some of the analyte test strips 401A that are adjacent to spacer 654, longitudinally offsetting some of the analyte test strips 601A by a width $\Delta w$.

In the embodiment shown, the insert 622 is shown comprising a disc shaped securing member 692 and spacer 654 extending distally from the securing member 692. It is noted that spacer 555 includes circular shaped surface 509, but surface 509 does not serve as a supporting surface to support analyte test strips. Securing member 692 comprises supporting surface 608 that is circularly shaped around spacer 555.

Spacer 654 is shorter in height than the distal tips of the analyte test strips 601A by a length $\Delta h2$ and creates an offset region 611 with a height of $\Delta h2$. Similar to the longitudinal offset described earlier, the height $\Delta h2$ of the offset region 611 serves to expose enough of the sides 610 of the analyte test strips that are adjacent to the spacer to enable a user's finger tip to grip the analyte test strip and displace it away from the other analyte test strip 401A. Example heights of the offset height $\Delta h2$ may range from, for example, 2 mm or more, such as 4 mm or more, and including 8 mm or more. The maximum of the offset height $\Delta h2$ depends on the longitudinal length of the cavity and the analtye test strips, and should not be large enough to allow an analyte test strip to be disposed on the distal surface 653 on the spacer 654 and yet remain completely in the cavity 688 of the container.

The offset region 611 and latitudinal offset $\Delta w$ created between analyte test strips adjacent to the spacer 654 enables a user to insert a finger tip within the offset region 611 and along the side 610 of an analyte test strip that is adjacent to the spacer 654 and to grip it so that it can be displaced away from the other analyte test strips 601A. Example widths $\Delta w$ of the offset region may range from, for example, 4 mm or more, such as 8 mm or more, including 10 mm or more.

The longitudinal distance between the distal surface 653 of the spacer 654 and the opening 607 of the container is shown as distance $\Delta h4$, which should be smaller in size than the length $\Delta h3$ of analyte test strips 401A. In this way, any analyte test strips that may be accidently disposed on the distal surface 653 of the spacer 654 are easily identifiable, and further, prevent the container from being closed (e.g., by cap 650).

Spacer 654 is cylindrically shaped with a distal circular surface 653 that is level and planar. Spacer 654 is shown extending from the center of the interior side 677 of the insert 622. Supporting surface 508 is planar and level, and located concentrically around the spacer 654 on the interior side 677 of the insert 622, shaped as a ring located concentrically around the outside of the spacer 654.

It should be appreciated that the illustrated embodiment is exemplary and the underlying principles are not limited to the illustrated embodiment. It should also be appreciated that, in some embodiments, more than one spacer may be implemented within a container. Furthermore, it should be appreciated that any variety of combinations of types, orientations, and shapes of supporting surfaces may be latitudinally offset by a spacer without compromising the underlying principles of the present disclosure. For example, the spacer may be ring shaped and include a supporting surface within the ring and a supporting surface outside the ring, with the ring providing a latitudinal offset between analyte test strips within the ring adjacent to the spacer and analyte test strips outside the ring adjacent to the spacer.

It should also be appreciated that supporting surfaces may be longitudinally offset in addition to being latitudinally offset without compromising the underlying principles of the present disclosure. The various embodiments described herein and shown in the figures are exemplary and should not be taken as limiting the scope of the present disclosure.

In some aspects of the present disclosure, methods of manufacturing analyte test strip containers having a cavity floor varies in height with respect to a longitudinal axis extending through the base and the opening of the container. In certain embodiments, the methods include forming a base to have a varying height with respect to a longitudinal axis. The forming of the base may include, for example, pressing, stamping, molding, etc. the base to include the appropriate contours to form the varying longitudinal height. The forming of the base may include molding the base to have a raised supporting surface that is longitudinally higher than another supporting surface. For example, the base may be formed to include an indentation or other protrusion that will extend in toward the cavity of the container to provide a raised supporting surface. It should be appreciate that the containers may be made from any variety of materials. For example, containers may be made from metals, metal alloys, polymers (e.g., hard plastics), or any other suitable material or combination of materials. should be appreciated that the supporting surfaces may be molded or otherwise formed to include various combinations of types, shapes and orientations as previously described above.

In certain embodiments, the methods comprise disposing analyte test strips within the container such that some analyte test strips are at a different height than other analyte test strips within the container. For example, a first plurality of test strips may be disposed on a first supporting surface that is longitudinally offset from a second supporting surface supporting a second plurality of test strips.

In certain embodiments, the methods comprise providing a desiccant within the container. The desiccant may be provided in a variety of manners—e.g., as an interior lining of one or more sidewalls, base and/or cap; as a desiccant element that is placed within the container. In certain embodiments, the desiccant is provided within the insert. For example, the desiccant may be lined on the insert (e.g., interior side of the insert, etc.). In some instances, the methods comprise sealing the container. For example, the container may include a cap that closes the opening of the cavity and seals the container. The seal may be made out of a material that acts as a barrier to water vapor or moisture.

In some aspects of the present disclosure, methods of making analyte test strip container systems are provided. The methods may comprise providing an analyte test strip container that supports analyte test strips at an approximately same longitudinal height within the containers, or otherwise positioned in a manner that makes them difficult to grab when generally full. For example, the analyte test strip containers may include generally planar and level bases that provide for a cavity floor that does not have varying heights with respect to the longitudinal axis of the container (e.g., analyte test strip containers in the prior art embodiments described above for FIGS. 1-3). Thus, without the inserts, the analyte test strip containers store all of the analyte test strips in the container at approximately the same height longitudinally. The test strips act collectively as a sort of barrier or surface that prevents the user from easily grabbing a test strip.

The methods also comprise situating an insert within the cavity of the analyte test strip container so that a proximal side of the insert is facing the base of the container, and an interior side of the insert faces the opening of the cavity. In certain embodiments, the interior side of the insert forms all of the cavity floor. In other embodiments, the cavity floor also comprises part of the interior side of the base that is exposed and not covered by the insert. The interior side of the insert may include one or more supporting surfaces to support a respective plurality of analyte test strips. Further, for embodiments where the cavity floor also comprises an exposed part of the interior side of the base, the interior side of the base that is exposed may include one or more supporting surfaces. It should be appreciated that the supporting surfaces may be any variety of combinations of types, shapes, and orientations, as previously described above.

In certain embodiments, the methods comprise disposing analyte test strips within the container such that some analyte test strips are at a different height than other analyte test strips within the container. For example, a first plurality of test strips may be disposed on a first supporting surface that is longitudinally offset from a second supporting surface supporting a second plurality of test strips.

In certain embodiments, the methods comprise providing a desiccant within the container. The desiccant may be provided in a variety of manners—e.g., as an interior lining of one or more sidewalls, base and/or cap; as a desiccant element that is placed within the container. In certain embodiments, the desiccant is provided within the insert. For example, the desiccant may be lined on the insert (e.g., interior side of the insert, etc.). In some instances, the methods comprise sealing the container. For example, the container may include a cap that closes the opening of the cavity and seals the container. The seal may be made out of a material that acts as a barrier to water vapor or moisture.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

That which is claimed is:

1. An analyte test strip container system comprising:
a container having a base, one or more sidewalls extending from the base, a cavity having an opening at a distal end and the base at the proximal end, and a cap at the distal end, wherein the cap fits over the opening to close the container and provide a sealed environment inside the container;
an insert comprising a proximal end and an interior side, wherein the insert is sized to fit within the opening and to situate within the cavity such that the proximal end of the insert is adjacent the base and the interior side of the insert forms a cavity floor that varies in height with respect to a longitudinal axis extending through the base and the opening of the container; and
a plurality of analyte test strips each having a distal end and a proximal end, placed inside the container, wherein the proximal end of the plurality of analyte test strips is in contact with the cavity floor, wherein the cavity floor holds at least one of the analyte test strips so that the distal end of the analyte test strip is at a different height with respect to the distal end of another analyte test strip of the plurality of analyte test strips, and wherein the plurality of analyte test strips are of the same length, wherein the distal end of the plurality of analyte test strips does not extend beyond the distal end of the cavity.

2. The analyte test strip container system of claim 1, wherein the cavity floor comprises a first supporting surface to support a first analyte test strip of the plurality of analyte test strips and a second supporting surface to support a second analyte test strip of the plurality of analyte test strips.

3. The analyte test strip container system of claim 2, wherein the interior side of the insert forms all of the cavity floor and comprises the first and second supporting surfaces.

4. The analyte test strip container system of claim 3, wherein the first supporting surface and second supporting surface are longitudinally offset in height with respect to the longitudinal axis.

5. The analyte test strip container system of claim 4, wherein the first supporting surface and second supporting surfaces are planar and level.

6. The analyte test strip container system of claim 4, wherein at least one of the first supporting surface and the second supporting surface is planar and angled.

7. The analyte test strip container system of claim 4, wherein at least one of the first supporting surface and the second supporting surfaces are non-planar.

8. The analyte test strip container system of claim 4, wherein the second supporting surface is circular shaped and raised with respect to the first supporting surface, and wherein the first supporting surface is ring shaped concentrically around the second supporting surface.

9. The analyte test strip container system of claim 4, wherein the second supporting surface comprises a ring shaped surface that is raised with respect to the first supporting surface.

10. The analyte test strip container system of claim 4, wherein the second supporting surface comprises a polygonal shaped surface that is raised with respect to the first supporting surface.

11. The analyte test strip container system of claim 4, wherein the base is circular and the container is a cylindrical shaped vial with one sidewall.

12. The analyte test strip container system of claim 4, wherein the longitudinal offset is at least 4 mm.

13. The analyte test strip container system of claim 1, wherein the interior side of the insert forms all of the cavity floor, and wherein the interior side of the insert comprises a first supporting surface to support a first analyte test strip of the plurality of analyte test strips and a spacer to provide a latitudinal offset for a second analyte test strip of the plurality of analyte test strips that are adjacent to the spacer, the latitudinal offset with respect to a latitudinal axis, the latitudinal axis perpendicular to the longitudinal axis.

14. The analyte test strip container system of claim 1, wherein the interior side of the insert forms all of the cavity floor, and wherein the interior side of the insert comprises:
a first supporting surface to support a first analyte test strip of the plurality of analyte test strips;
a second supporting surface to support a second analyte test strip of the plurality of analyte test strips; and
a spacer to provide a latitudinal offset for the first analyte test strip and the second analyte test strip that are adjacent to the spacer, the latitudinal offset with respect to a latitudinal axis, the latitudinal axis perpendicular to the longitudinal axis.

15. A method comprising:
providing an analyte test strip container having a base, one or more sidewalls extending from the base, a cavity having an opening at a distal end and the base at the proximal end, and a cap at the distal end, wherein the cap fits over the opening to close the container and provide a sealed environment inside the container;
situating a solid insert comprising a proximal end and an interior side within the cavity such that the proximal end of the insert is adjacent the base and the interior side of the insert forms a cavity floor having a varying height with respect to a longitudinal axis extending through the base and the opening of the container; and
placing a plurality of analyte test strips, each having a distal end and a proximal end, inside the container, wherein the proximal end of the plurality of analyte test strips is in contact with the cavity floor, wherein the cavity floor holds at least one of the analyte test strips so that the distal end of the analyte test strip is at a different height with respect to the distal end of another analyte test strip of the plurality of analyte test strips, and wherein the plurality of analyte test strips are of the same length, wherein the distal end of the plurality of analyte test strips does not extend beyond the distal end of the cavity.

16. The method of claim 15, wherein the cavity floor comprises a first supporting surface to support a first plurality of analyte test strips and a second supporting surface to support a second plurality of analyte test strips.

17. The method of claim 16, wherein the interior side of the insert forms all of the cavity floor and comprises the first and second supporting surfaces.

18. The method of claim 17, wherein the first supporting surface and second supporting surface are longitudinally offset in height with respect to the longitudinal axis.

19. The method of claim 18, wherein the first supporting surface and second supporting surfaces are planar and level.

20. The method of claim 15, wherein the insert covers a portion of an interior side of the base leaving an uncovered portion of the interior side of the base, the interior side of the base comprising a first supporting surface, and wherein the interior side of the insert comprises a second supporting surface.

21. The method of claim 20, wherein the first supporting surface and second supporting surface are longitudinally offset in height with respect to the longitudinal axis.

22. The method of claim 21, wherein the first supporting surface and second supporting surfaces are planar and level.

23. The method of claim 22, wherein the second supporting surface is circular shaped and raised with respect to the first supporting surface, wherein the first supporting surface is ring shaped concentrically around the second supporting surface.

24. The method of claim 16, wherein the second supporting surface is circular shaped and raised with respect to the first supporting surface, wherein the first supporting surface is ring shaped concentrically around the second supporting surface.

* * * * *

UNITED STATES PATENT AND TRADEMARK OFFICE
CERTIFICATE OF CORRECTION

PATENT NO. : 8,757,386 B2
APPLICATION NO. : 12/895502
DATED : June 24, 2014
INVENTOR(S) : Rush et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this
Twenty-eighth Day of June, 2016

Michelle K. Lee
*Director of the United States Patent and Trademark Office*